(12) United States Patent
Takahashi et al.

(10) Patent No.: US 9,820,661 B2
(45) Date of Patent: Nov. 21, 2017

(54) BIOLOGICAL INFORMATION DETECTION APPARATUS

(71) Applicant: Seiko Epson Corporation, Shinjuku-ku (JP)

(72) Inventors: Yusuke Takahashi, Matsumoto (JP); Hideto Yamashita, Suwa (JP); Masao Kuroda, Shiojiri (JP); Ichiro Aoshima, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 139 days.

(21) Appl. No.: 14/205,202

(22) Filed: Mar. 11, 2014

(65) Prior Publication Data

US 2014/0275949 A1     Sep. 18, 2014

(30) Foreign Application Priority Data

Mar. 18, 2013   (JP) .................................. 2013-054494
Mar. 18, 2013   (JP) .................................. 2013-054495

(51) Int. Cl.
*A61B 5/02*      (2006.01)
*A61B 5/024*     (2006.01)
(Continued)

(52) U.S. Cl.
CPC ........ *A61B 5/02438* (2013.01); *A61B 5/0059* (2013.01); *A61B 5/02416* (2013.01);
(Continued)

(58) Field of Classification Search
None
See application file for complete search history.

(56) References Cited

U.S. PATENT DOCUMENTS 5,766,131 A    6/1998   Kondo et al.
6,605,045 B2   8/2003   Ohsaki et al.
(Continued)

FOREIGN PATENT DOCUMENTS

EP    0 756 849 A1    2/1997
EP    0 941 694 A1    9/1999
(Continued)

OTHER PUBLICATIONS

European search report, dated May 28, 2014, of the corresponding European Application No. 14159853.2. 6 pgs.
(Continued)

*Primary Examiner* — Eric Winakur
*Assistant Examiner* — Marjan Fardanesh
(74) *Attorney, Agent, or Firm* — Kilpatrick Townsend & Stockton LLP

(57) ABSTRACT

A biological information detection apparatus includes a detection unit which has a light receiving unit receiving light from a subject, a light transmitting member which is provided on a housing surface side in contact with the subject of the biological information detection apparatus, transmits light from the subject, and has a convex portion in contact with the subject to give a pressing force when measuring biological information of the subject, and a pressing force suppression unit which is disposed in periphery of the convex portion on or above the housing surface and suppresses the pressing force given to the subject by the convex portion. A groove portion is provided between the convex portion of the light transmitting member and the pressing force suppression unit.

19 Claims, 26 Drawing Sheets

(51) Int. Cl.
*A61B 5/00* (2006.01)
*A61B 5/11* (2006.01)

(52) U.S. Cl.
CPC ............ *A61B 5/681* (2013.01); *A61B 5/6824* (2013.01); *A61B 5/6843* (2013.01); *A61B 5/7207* (2013.01); *A61B 5/11* (2013.01); *A61B 2560/0406* (2013.01)

(56) References Cited

U.S. PATENT DOCUMENTS

| | | |
|---|---|---|
| 2004/0062056 A1 | 4/2004 | Heine et al. |
| 2007/0270702 A1 | 11/2007 | Ahola |
| 2008/0144004 A1 | 6/2008 | Rosenthal |
| 2011/0092832 A1 | 4/2011 | Onoe et al. |
| 2011/0166457 A1 | 7/2011 | Sato et al. |
| 2011/0260176 A1 | 10/2011 | Onoe et al. |
| 2013/0267854 A1 | 10/2013 | Johnson et al. |

FOREIGN PATENT DOCUMENTS

| | | |
|---|---|---|
| EP | 1 447 044 A1 | 8/2004 |
| EP | 2 020 202 A2 | 2/2009 |
| EP | 2 020 202 A3 | 2/2009 |
| EP | 2 520 222 A1 | 11/2012 |
| JP | 57-093039 A | 6/1982 |
| JP | 2001-353133 A | 12/2001 |
| JP | 2004-188224 A | 7/2004 |
| JP | 2005-270543 A | 10/2005 |
| JP | 2008-043515 A | 2/2008 |
| JP | 2008-086705 A | 4/2008 |
| JP | 2008-237453 A | 10/2008 |
| JP | 2009-006070 A | 1/2009 |
| JP | 2009-200433 A | 9/2009 |
| JP | 2009-201919 A | 9/2009 |
| JP | 2011-139725 A | 7/2011 |
| JP | 5031894 B2 | 7/2012 |
| TW | 200722047 A | 6/2007 |
| WO | 2009/139029 A1 | 11/2009 |

OTHER PUBLICATIONS

Extended European search report, dated Sep. 23, 2014, of the corresponding European Application No. 14159853.2. 14 pgs.
Extended European search report, dated May 20, 2014, of the corresponding European Application No. 14159850.8.
Final Office Action in related U.S. Appl. No. 14/205,154 dated Nov. 9, 2016 (22 pages).
Notice of Allowance dated Jul. 13, 2017 in related U.S. Appl. No. 14/205,154, (17 pages).

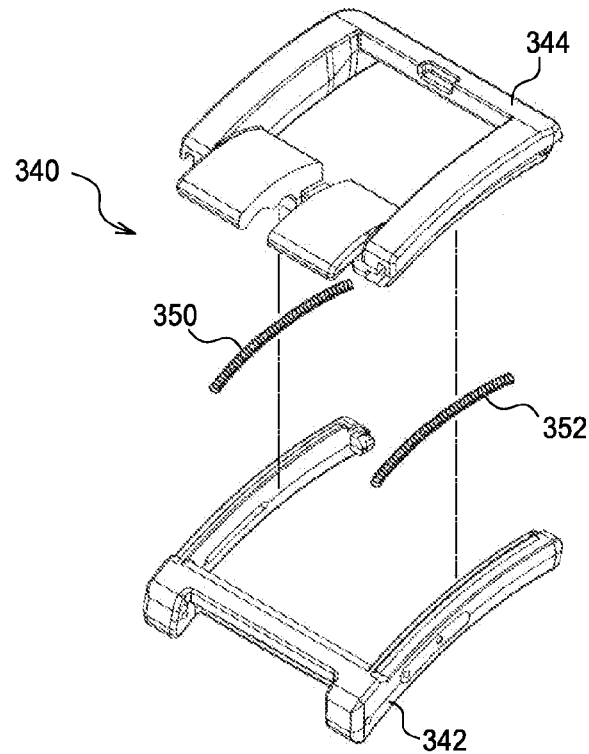
FIG. 2A
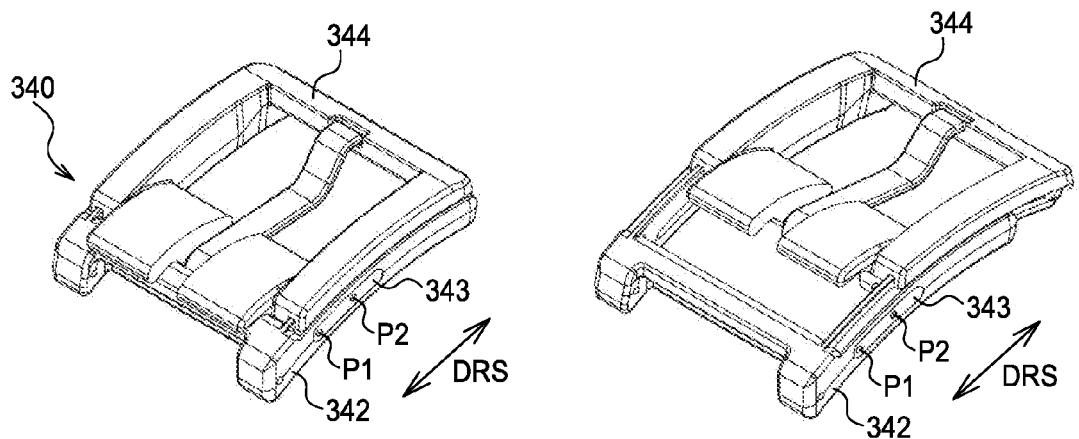
FIG. 2B
FIG. 2C

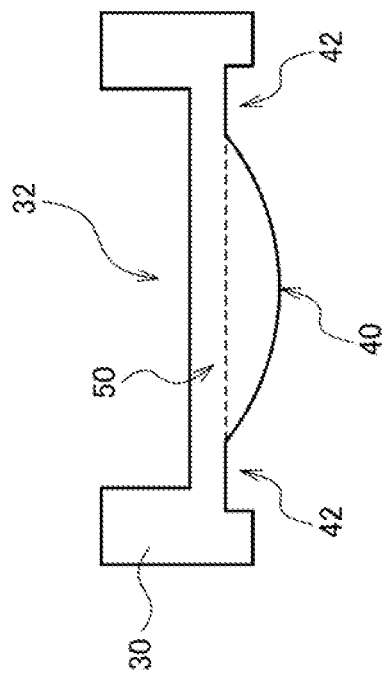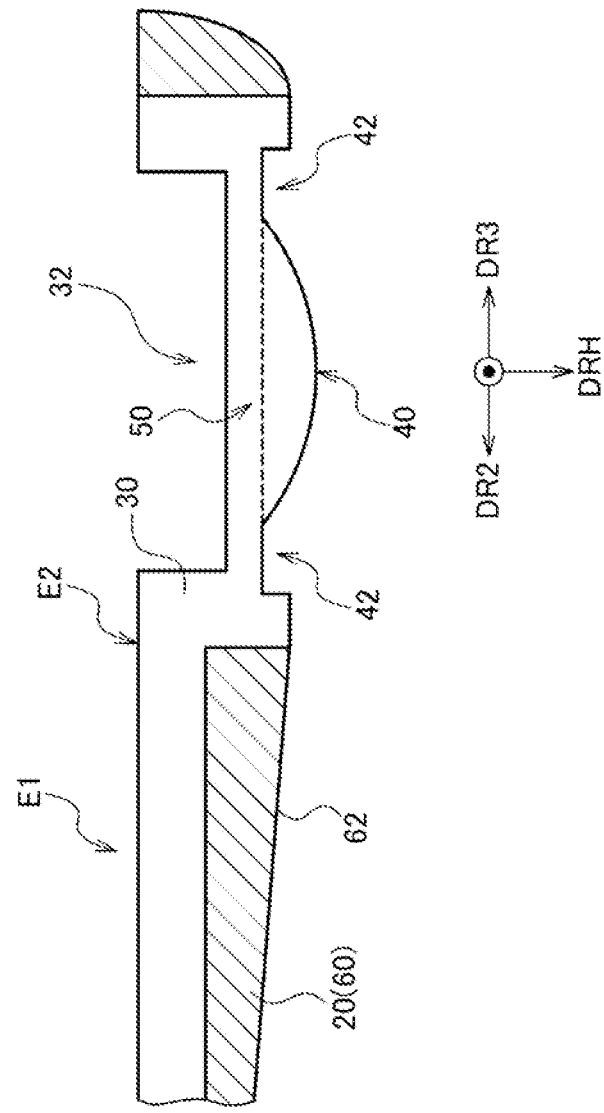
FIG.20A
FIG.20B

BIOLOGICAL INFORMATION DETECTION APPARATUS

CROSS-REFERENCE TO RELATED APPLICATION

The present application is based on and claims priority from Japanese Patent Application No. 2013-054494, filed Mar. 18, 2013, and Japanese Patent Application No. 2013-054495, filed Mar. 18, 2013, the disclosures of which are incorporated herein by reference.

BACKGROUND

1. Technical Field

The present invention relates to a biological information detection apparatus and the like.

2. Related Art

A biological information detection apparatus which detects biological information, such as a pulse wave of a human, is hitherto known. JP-A-2011-139725 and JP-A-2009-201919 disclose a pulsimeter of the related art which is an example of the biological information detection apparatus. The pulsimeter is put on, for example, an arm, a wrist, a finger, or the like, and detects pulsation resulting from heartbeat of a human body to measure a pulse rate.

The pulsimeter disclosed in JP-A-2011-139725 and JP-A-2009-201919 is a photoelectric pulsimeter, and a detection unit (pulse wave sensor) of the pulsimeter has a light emitting unit which emits light toward a subject (a region to be detected), and a light receiving unit which receives light (light having biological information) from the subject. In this pulsimeter, change in blood flow is detected as change in the amount of received light, thereby detecting a pulse wave. JP-A-2011-139725 discloses a pulsimeter which is put on a wrist, and JP-A-2009-201919 discloses a pulsimeter which is put on a finger.

In JP-A-2011-139725 and JP-A-2009-201919, a light transmitting member which transmits light from the light emitting unit or light from the subject is provided, and the light transmitting member has a contact surface with the subject (the skin of the wrist or the finger). Then, if a convex portion is provided on the contact surface of the light transmitting member, a pressing force is easily applied when coming into contact with the skin of the subject.

However, as a side effect, there is the effect of change in pressing force caused by shaking of the instrument of the biological information detection apparatus by body motion, motion (for example, clasp and unclasp operation) of the hand of a user on which the biological information detection apparatus is put. When change in pressing force is large, this means that a body motion noise component which is superimposed on a detection signal of the biological information is large.

For example, if the convex portion of the light transmitting member formed of a hard material comes into contact with a soft surface of a living body, such as skin, a flat portion around the convex portion and the surface of the living body are in a non-contact state or a weak contact state, or the like, and the contact state dynamically changes. If dynamic change in the contact state occurs, light intensity is likely to be optically generated, and if light enters the light receiving unit, light becomes noise having no correlation with a pulse component, and quality of a detection signal of the biological information is deteriorated.

In this biological information detection apparatus, it is desirable to make the amount of received light, which passes through the light transmitting member from the subject and enters the light receiving unit, as large as possible. It is also desirable to make the amount of light, which passes through the light transmitting member from the light emitting unit and is emitted toward the subject, as large as possible.

When the light transmitting member having the convex portion or the detection unit is embedded in the biological information detection apparatus, improvement of waterproof performance, ease of assembling, or the like becomes an important element.

SUMMARY

An aspect of the invention relates to a biological information detection apparatus including a detection unit which has a light receiving unit receiving light from a subject, a light transmitting member which is provided on a housing surface side in contact with the subject of the biological information detection apparatus, transmits light from the subject, and has a convex portion in contact with the subject to give a pressing force when measuring biological information of the subject, and a pressing force suppression unit which is disposed in periphery of the convex portion above the housing surface and suppresses the pressing force given to the subject by the convex portion, in which a groove portion is provided between the convex portion of the light transmitting member and the pressing force suppression unit.

Another aspect of the invention relates to a biological information detection apparatus including a detection unit which has a light receiving unit receiving light from a subject, and a light transmitting member which is provided on a housing surface side in contact with the subject of the biological information detection apparatus, and transmits light entering the light receiving unit from the subject, in which the light transmitting member has a convex portion, which comes into contact with the subject to give a pressing force when measuring biological information of the subject, on a first surface and has a concave portion at a position corresponding to the convex portion on a second surface on the rear side of the first surface.

BRIEF DESCRIPTION OF THE DRAWINGS

The invention will be described with reference to the accompanying drawings, wherein like numbers reference like elements.

FIGS. 2A to 2C are explanatory views of a connection of the biological information detection apparatus.

FIGS. 20A and 20B are explanatory views showing an example of the light transmitting member.

DESCRIPTION OF EXEMPLARY EMBODIMENTS

Figure 1A:
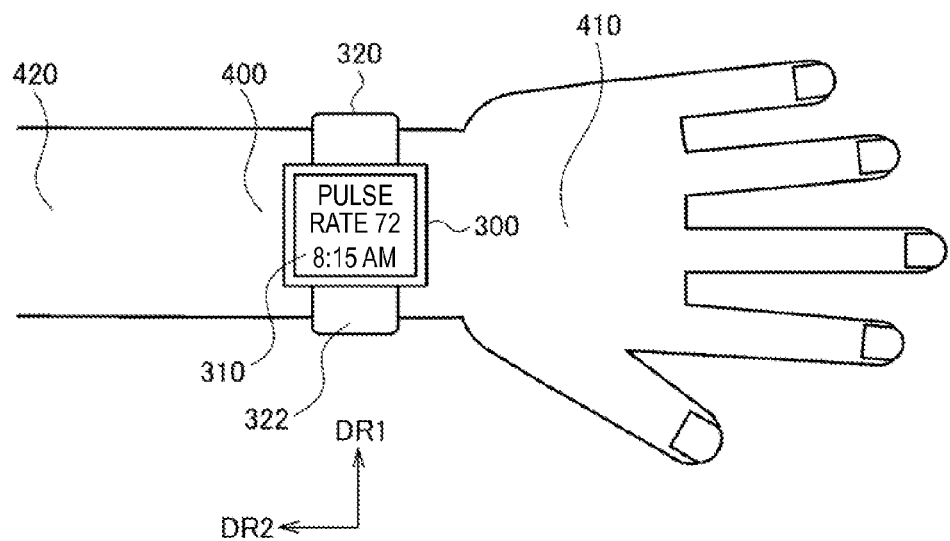
FIGS. 1A and 1B are appearance diagrams of a biological information detection apparatus of this embodiment.

According to some aspects of the invention, it is possible to provide a biological information detection apparatus or the like which can suppress deterioration of signal quality of a detection signal or the like due to change in a contact state or the like around a convex portion.

According to some aspects of the invention, it is possible to provide a biological information detection apparatus or the like which can improve waterproof, ease of assembling, or the like while suppressing deterioration of signal quality of a detection signal.

A biological information detection apparatus according to an embodiment of the invention includes a detection unit which has a light receiving unit receiving light from a subject, a light transmitting member which is provided on a housing surface side in contact with the subject of the biological information detection apparatus, transmits light from the subject, and has a convex portion in contact with the subject to give a pressing force when measuring biological information of the subject, and a pressing force suppression unit which is disposed in periphery of the convex portion above the housing surface and suppresses the pressing force given to the subject by the convex portion, in which a groove portion is provided between the convex portion of the light transmitting member and the pressing force suppression unit.

According to this embodiment, the convex portion of the light transmitting member comes into contact with the subject when measuring the biological information of the subject, light passing through the light transmitting member is received by the light receiving unit of the detection unit, thereby detecting the biological information of the subject. In this embodiment, the pressing force suppression unit which suppresses the pressing force given to the subject by the convex portion is disposed in periphery of the convex portion, and the groove portion is provided between the convex portion of the light transmitting member and the pressing force suppression unit. With this configuration, it becomes possible to suppress dynamic change in a contact state or the like around the convex portion and to cause a load to concentrate on the convex portion at the time of an initial pressing force or the like. Accordingly, it becomes possible to effectively suppress deterioration of signal quality of a detection signal or the like due to change in a contact state or the like.

In this embodiment, when the height of the convex portion in a direction orthogonal to the housing surface, the height of the pressing force suppression unit, and the height of the bottom surface of the groove portion are respectively HA, HB, and HC, HA>HB>HC.

With this configuration, the convex portion first comes into contact with the subject, and then the pressing force suppression unit comes into contact with the surface of the subject, thereby suppressing the pressing force of the convex portion, and even when the convex portion and the pressing force suppression unit come into contact with the subject, preventing the bottom surface of the groove portion from coming into contact with the surface of the subject.

In this embodiment, when the difference between the height HA of the convex portion and the height HC of the bottom surface of the groove portion is $\Delta h2$, $\Delta h2 > 0.5$ mm.

In this way, $\Delta h2$ corresponding to the depth of the groove portion becomes greater than 0.5 mm, whereby, when the bottom surface of the groove portion and the subject are in contact with each other or in a weak contact state, it is possible to suppress deterioration of signal quality of a detection signal or the like due to stray light or the like in this portion.

In this embodiment, the groove portion may be provided over the entire circumference of the convex portion.

With this configuration, for example, it is possible to suppress the occurrence of dynamic change in a contact state over the entire circumference of the convex portion, thereby realizing stable improvement of signal quality of a detection signal.

In this embodiment, the bottom surface of the groove portion may be the surface of the light transmitting member.

With this configuration, it becomes possible to form the bottom surface of the groove portion effectively utilizing the surface of a part of the light transmitting member.

In this embodiment, the light transmitting member may have the convex portion at least a part of which protrudes toward the subject, and a body portion which is provided on the downward side of the convex portion opposite to the subject, and the bottom surface of the groove portion may be the surface of the body portion.

With this configuration, it becomes possible to form the bottom surface of the groove portion effectively utilizing the surface of a part of the body portion of the light transmitting member.

In this embodiment, the body portion may be formed to extend from the position of the convex portion downward of a cover member of the housing surface, and the pressing force suppression surface of the pressing force suppression unit may be the surface of the cover member.

With this configuration, it becomes possible to form the pressing force suppression surface effectively utilizing the cover member above the body portion.

In this embodiment, when the amount of change in pressing force of the convex portion with respect to a load by a load mechanism generating the pressing force of the convex portion is defined as the amount of change in pressing force, the pressing force suppression unit may suppress the pressing force given to the subject by the convex portion such that the amount of change in pressing force in a second load range in which the load of the load mechanism is greater than FL1 becomes smaller than the amount of change in pressing force in a first load range in which the load of the load mechanism is 0 to FL1.

In this way, if the pressing force of the convex portion is suppressed such that the amount of change in pressing force in the second load range becomes smaller than the amount of change in pressing force in the first load range, it becomes possible to suppress the pressing force given to the subject by the convex portion to reduce change in pressing force or the like while giving an appropriate initial pressing force to the subject by the convex portion.

In this embodiment, the pressing force suppression unit may have a pressing force suppression surface which expands outward from around the convex portion.

With this configuration, it becomes possible to suppress the pressing force given to the subject by the convex portion equally and efficiently using the pressing force suppression surface which expands outward from around the convex portion.

In this embodiment, when a position away from the position of the convex portion at a first distance in a predetermined direction is a first position, a position away from the position of the convex portion at a second distance longer than the first distance in the predetermined direction is a second position, the height of the pressing force suppression surface in a direction orthogonal to the housing surface at the first position is HS1, and the height of the pressing force suppression surface in the direction orthogonal to the housing surface at the second position is HS2, HS1>HS2.

If the relationship of HS1>HS2 is established, it is possible to effectively suppress the occurrence of change in pressing force of the convex portion or the like due to change in the contact state with the subject or the like at a location away from the convex portion.

In this embodiment, the pressing force suppression surface may be inclined such that the height in the direction orthogonal to the housing surface decreases toward a predetermined direction from the position of the convex portion.

If the inclination is provided, since the height of the pressing force suppression surface in the direction orthogonal to the housing surface decreases toward the side away from the convex portion, it is possible to reduce adverse effects due to change in the contact state with the subject or the like at a location away from the convex portion.

A biological information detection apparatus according to another embodiment of the invention includes a detection unit which has a light receiving unit receiving light from a subject, and a light transmitting member which is provided on a housing surface side in contact with the subject of the biological information detection apparatus, and transmits light entering the light receiving unit from the subject, in which the light transmitting member has a convex portion, which comes into contact with the subject to give a pressing force when measuring biological information, on a first surface and has a concave portion at a position corresponding to the convex portion on a second surface on the rear side of the first surface.

According to this embodiment, the convex portion of the light transmitting member comes into contact with the subject when measuring the biological information of the subject, and light passing through the light transmitting member is received by the light receiving unit of the detection unit, thereby detecting the biological information of the subject. In this embodiment, the convex portion which comes into contact with subject to give the pressing force is provided on the first surface of the light transmitting member, and the concave portion is provided on the second surface of the light transmitting member. If the concave portion is provided, the thickness of the light transmitting member at a location corresponding to the convex portion is substantially thinned so as to suppress the amount of attenuation of light, making it possible to suppress deterioration of signal quality of a detection signal. It also becomes possible to expect improvement of waterproof performance, ease of assembling, or the like.

In this embodiment, the light receiving unit of the detection unit may receive light from the subject which passes through the convex portion and the concave portion of the light transmitting member.

With this configuration, since it is possible to shorten an optical path when incoming light from the subject to the light receiving unit passes through the light transmitting member, it becomes possible to decrease the amount of attenuation of light when incoming light passes through the light transmitting member, and to suppress deterioration of signal quality of a detection signal or the like.

In this embodiment, the detection unit may have a light emitting unit which emits light to the subject, and the light emitting unit may emit light which passes through the convex portion and the concave portion of the light transmitting member.

With this configuration, since it is possible to shorten an optical path when outgoing light from the light emitting unit to the subject passes through the light transmitting member, it becomes possible to decrease the amount of attenuation of light when outgoing light passes through the light transmitting member, and to suppress deterioration of signal quality of a detection signal or the like.

In this embodiment, the light transmitting member may have a flat portion formed around the convex portion on the first surface.

In this embodiment, the convex portion may be formed on the entire first surface of the light transmitting member.

With this configuration, it is possible to stabilize the contact state of the convex portion and the surface of the subject, and to improve signal quality of a detection signal or the like.

In this embodiment, the biological information detection apparatus may further include a pressing force suppression unit which is disposed in periphery of the convex portion above the housing surface and suppresses the pressing force given to the subject by the convex portion.

With this configuration, for example, in a use range or the like in which the biological information is measured by the biological information detection apparatus, the pressing force by the convex portion is suppressed by the pressing force suppression unit, making it possible to minimize change in pressing force and to achieve reduction of a noise component or the like.

In this embodiment, the light transmitting member may have the convex portion at least a part of which protrudes toward the subject, and a body portion which is provided on the downward side of the convex portion opposite to the subject, and the convex portion may be provided on the second surface of the body portion.

With this configuration, it becomes possible to form the concave portion effectively utilizing the second surface of the body portion of the light transmitting member.

In this embodiment, the biological information detection apparatus may further include a pressing force suppression unit which is disposed in periphery of the convex portion above the housing surface and suppresses the pressing force given to the subject by the convex portion, in which the body portion may be formed to extend from the position of the convex portion downward of a cover member of the housing surface, and the pressing force suppression surface of the pressing force suppression unit may be the surface of the cover member.

With this configuration, it becomes possible to form the pressing force suppression surface effectively using the cover member above the body portion.

In this embodiment, the biological information detection apparatus may further include a diaphragm unit which is provided between the light transmitting member and the detection unit, between the light transmitting member and the subject, or inside the light transmitting member, and narrows light from the subject in an optical path between the subject and the detection unit.

If the diaphragm unit is provided, even when stray light occurs due to change in the contact state of the contact surface with the subject or the like, it is possible to suppress the entrance of stray light to the light receiving unit and to detect appropriate biological information.

In this embodiment, the detection unit may include a light emitting unit which emits light to the subject, the light transmitting member may transmit light from the light emitting unit, and the biological information detection apparatus may further include a light shielding unit which is provided between the light receiving unit and the light emitting unit.

If the light shielding unit is provided, it is possible to suppress the entrance of direct light from the light emitting unit to the light receiving unit and to detect appropriate biological information.

In this embodiment, the convex portion may have a curved shape in at least a portion in contact with the subject.

With this configuration, it becomes possible to give a pressing force to the subject by the convex portion in a stable contact state.

In this embodiment, a pulse wave may be detected as the biological information.

However, the biological information to be detected by the biological information detection apparatus is not limited to the pulse wave.

Hereinafter, this embodiment will be described. This embodiment described below is not unduly limited to the disclosure of the invention described in the appended claims. All configurations described in this embodiment are not necessarily the essential components of the invention.

1. Biological Information Detection Apparatus

FIG. 1A is an appearance diagram showing an example of a biological information detection apparatus (biological information measuring apparatus) of this embodiment. The biological information detection apparatus is a timepiece type pulsimeter, and has a main body 300 and bands 320 and 322 (wrist bands) for attaching the biological information detection apparatus of a wrist 400 of the subject. The main body 300 as an apparatus main body is provided with a display unit 310 which displays various kinds of information, a pulse wave sensor (a sensor having a detection unit, a light transmitting member, and the like), a processing unit which performs various kinds of processing, and the like. The measured pulse rate or time is displayed on the display unit 310. In FIG. 1A, a circumferential direction of the wrist 400 (or an arm) is defined as a first direction DR1, and a direction from a hand 410 to a lower arm 420 is defined as a second direction DR2.

Figure 1B:
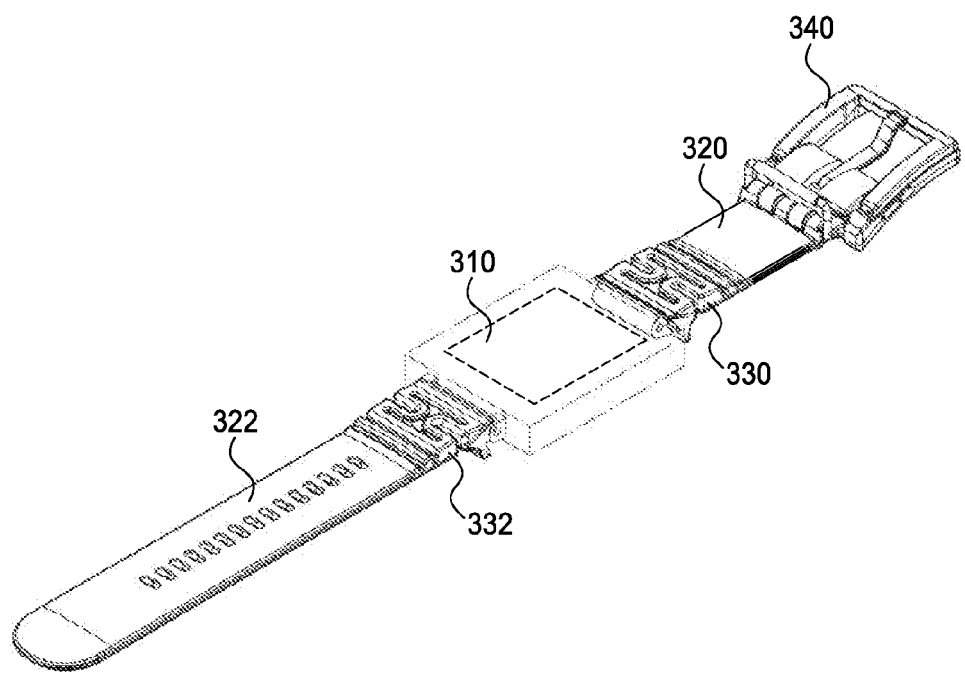

FIG. 1B is an appearance diagram showing a detailed configuration example of the biological information detection apparatus. The bands 320 and 322 are connected to the main body 300 through extension/contraction portions 330 and 332. The extension/contraction portions 330 and 332 are configured to be deformed along the first direction DR1, the second direction DR2, and the like of FIG. 1A. A connection 340 is connected to one end of the hand 320. The connection 340 corresponds to a buckle in a timepiece, and a band hole into which a rod of the buckle is inserted is formed in the opposite band 322.

As shown in FIG. 2A, the connection 340 has a fixing member 342 which is fixed to the band 320, a slide member 344, or springs 350 and 352 as an elastic member. As shown in FIGS. 2B and 2C, the slide member 344 is slidably attached to the fixing member 342 along a slide direction DRS, and the springs 350 and 352 generate a tensile force during sliding. A load mechanism of this embodiment is realized by the springs 350 and 352, the extension/contraction portions 330 and 332, the bands 320 and 322, or the like.

An indicator 343 is provided in the fixing member 342, and a scale for indicating an appropriate slide range is attached to the indicator 343. Specifically, points P1 and P2 which indicate an appropriate slide range (pressing force range) are attached to the indicator 343. If the end portion on the band 320 side of the slide member 344 is located within the range of the points P1 and P2, it is ensured that the slide member is within an appropriate slide range (pressing force range), and an appropriate tensile force is applied. A user inserts the rod of the connection 340 corresponding to a buckle into the band hole of the band 322 so as to be within the appropriate slide range, and puts the biological information detection apparatus on his/her wrist. With this, it is ensured to some extent that the pressing force of the pulse wave sensor (a convex portion of a light transmitting member) to the subject becomes an assumed appropriate pressing force. The details of the structure of the biological information detection apparatus shown in FIGS. 1A to 2C are disclosed in JP-A-2012-90975.

In FIGS. 1A to 2C, although a case where the biological information detection apparatus is a timepiece type pulsimeter which is put on a wrist has been described as an example, this embodiment is not limited thereto. For example, the biological information detection apparatus of this embodiment may be a biological information detection apparatus which is put on a region (for example, a finger, an upper arm, a chest, or the like) other than a wrist to detect (measure) biological information. The biological information to be detected by the biological information detection apparatus is not limited to a pulse wave (pulse rate), and an apparatus which detects biological information (for example, a blood oxygen saturation level, body temperature, heartbeat, or the like) other than the pulse wave may be used.

Figure 3:
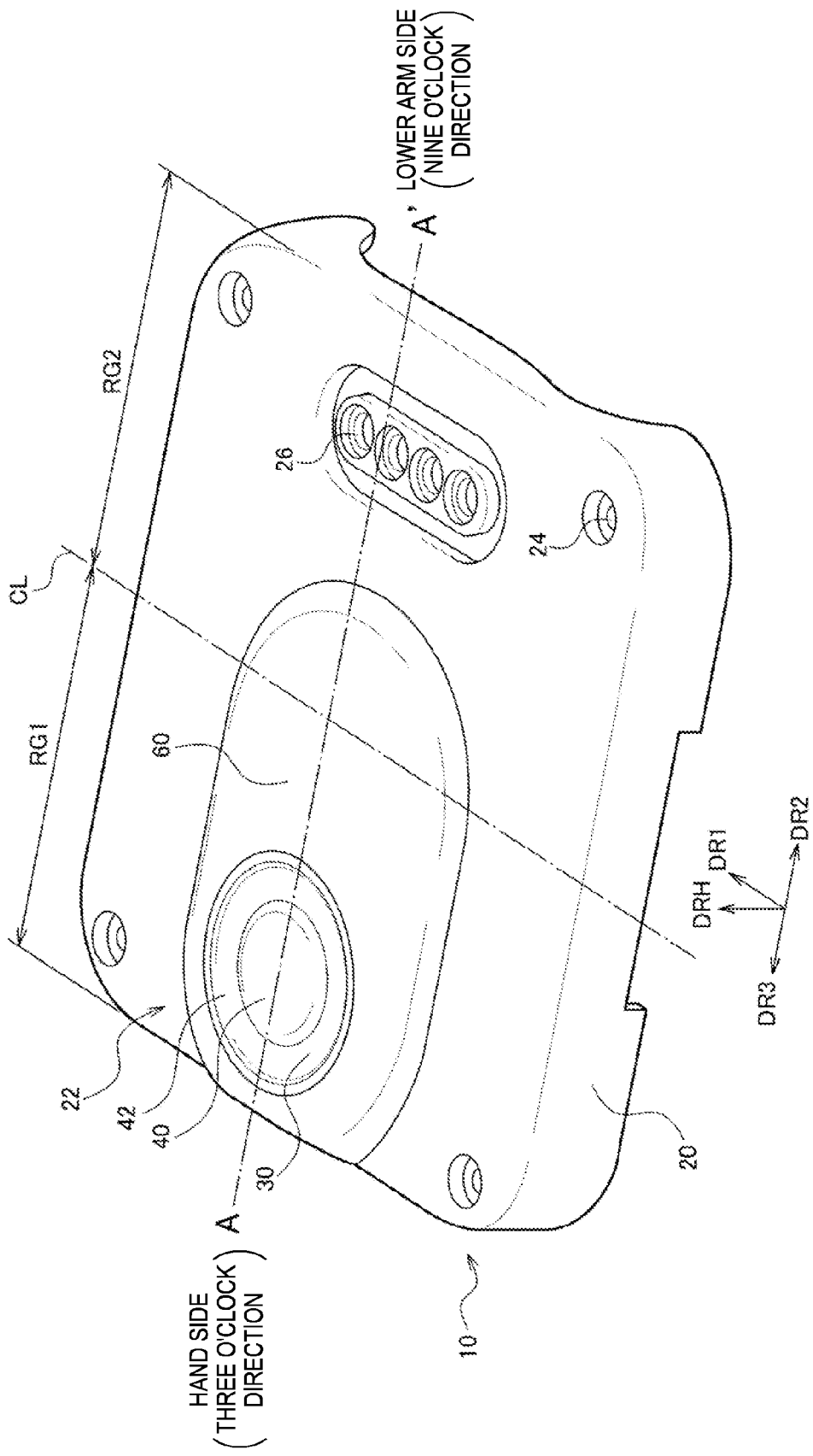
FIG. 3 is a perspective view of a rear lid of a main body of the biological information detection apparatus.
Figure 4:
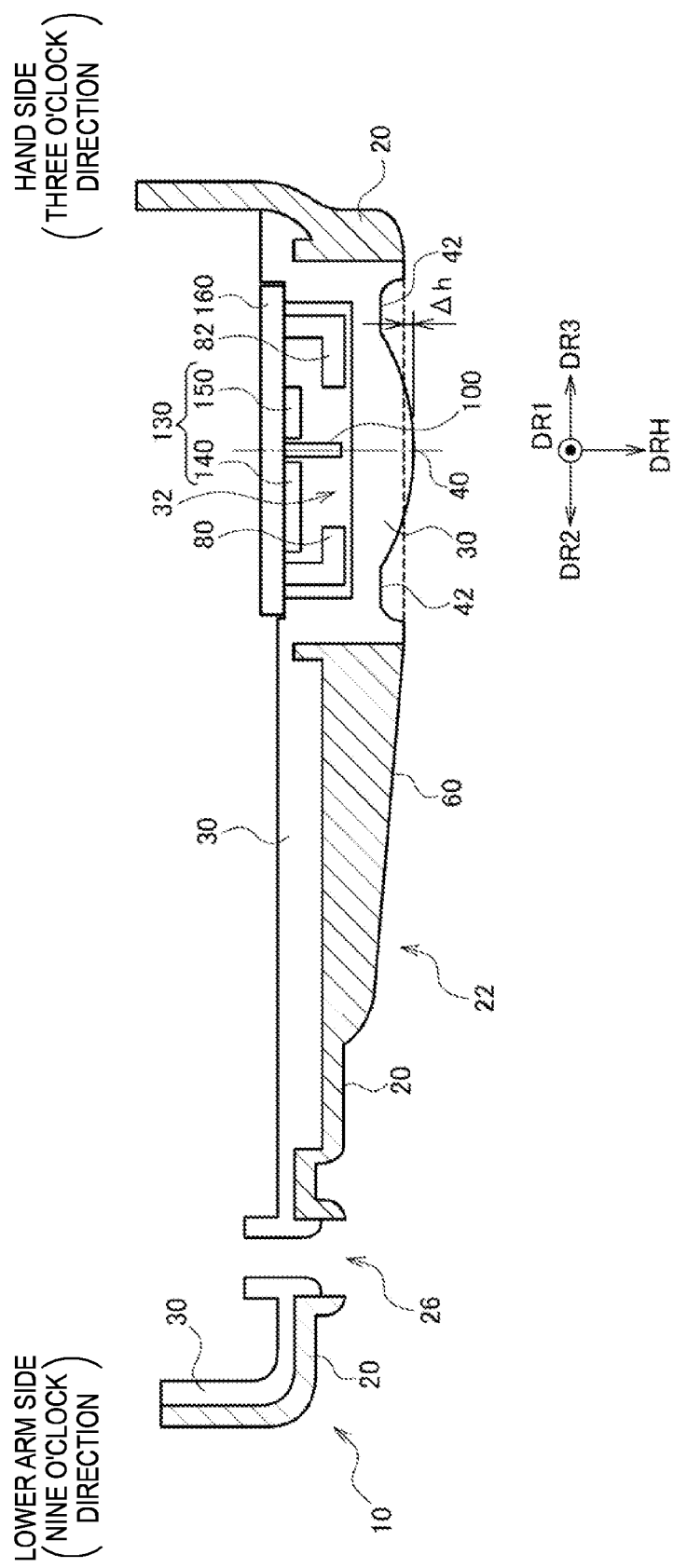
FIG. 4 is a sectional view of the rear lid.

FIG. 3 is a perspective view showing a configuration example of a rear lid 10 provided on the rear side of the main body 300 of the biological information detection apparatus, and FIG. 4 is a sectional view taken along the line IV-IV of FIG. 3. The rear lid 10 is constituted by a cover member 20 and a light transmitting member 30, and a housing surface 22 (rear surface) on the rear side of the main body 300 is constituted by the rear lid 10.

The light transmitting member 30 is provided on the housing surface 22 side in contact with the subject of the biological information detection apparatus, and transmits light from the subject. The light transmitting member 30 comes into contact with the subject when measuring the biological information of the subject. For example, a convex portion 40 of the light transmitting member 30 comes into contact with the subject. While it is preferable that the surface shape of the convex portion 40 is a curved shape (spherical shape), the invention is not limited thereto, and various shapes may be used. The light transmitting member 30 may be transparent to the wavelength of light from the subject, and a transparent material may be used, or a colored material may be used.

As shown in FIG. 4, the cover member 20 is formed so as to cover the light transmitting member 30. While the light transmitting member 30 has a light transmitting property, the cover member 20 is a non-light transmitting member having no light transmitting property. For example, the light transmitting member 30 is formed of transparent resin (plastic), and the cover member 20 is formed of resin of a predetermined color, such as black. The non-light transmitting property means the property of a material which does not transmit light of a wavelength to be detected by the biological information detection apparatus.

As shown in FIGS. 3 and 4, a part of the light transmitting member 30 is exposed from an opening of the cover member 20 toward the subject, and the convex portion 40 is formed in the exposed portion. Accordingly, when measuring the biological information, the convex portion 40 formed in the exposed portion comes into contact with the subject (for example, the skin of the wrist of the user). In FIGS. 3 and 4, a detection window of the biological information detection apparatus is constituted by the convex portion 40 formed in the exposed portion. In FIG. 4, the light transmitting member 30 is also provided in a portion other than the detection window, that is, a rear side portion of the cover member 20 (pressing force suppression unit 60). This embodiment is not limited thereto, and the light transmitting member 30 may be provided in the portion of the detection window.

As shown in FIG. 4, a groove portion 42 for suppressing change in pressing force or the like is provided around the convex portion 40. When a surface of the light transmitting member 30 on the side on which the convex portion 40 is provided is defined as a first surface, the light transmitting member 30 has a concave portion 32 at a position corresponding to the convex portion 40 on a second surface on the rear side of the first surface. The rear lid 10 is provided with a screw hole 24 for fastening the rear lid 10, a terminal hole 26 for connecting a terminal for signal transfer or power supply, and the like.

As shown in FIG. 3, when the housing surface 22 (rear surface) of the biological information detection apparatus is divided into a first region RG1 and a second region RG2 by a central line CL along the first direction DR1, the convex portion 40 is provided in the first region RG1. For example, in the case of the biological information detection apparatus shown in FIG. 1A which is put on the wrist, the first region RG1 is a hand-side region (a three o'clock direction in a timepiece), and the second region RG2 is a lower arm-side region (a nine o'clock direction in a timepiece). In this way, the convex portion 40 of the light transmitting member 30 is provided in the first region RG1 close to the hand on the housing surface 22. With this, since the convex portion 40 is arranged at a location where there is small change in the diameter of the arm, it is possible to suppress change in pressing force or the like.

The convex portion 40 comes into contact with the subject when measuring the biological information of the subject and gives a pressing force (pressure). Specifically, when the user puts the biological information detection apparatus on his/her wrist to detect biological information, such as a pulse wave, the convex portion 40 comes into contact with the skin of the wrist of the user to give the pressing force. The pressing force is generated by the load of the load mechanism described in FIGS. 1A to 2C.

On the housing surface 22 of the biological information detection apparatus, a pressing force suppression unit 60 which suppresses the processing force to be given to the subject (the skin of the wrist) by the convex portion 40 is provided. In FIGS. 3 and 4, the pressing force suppression unit 60 is provided so as to surround the convex portion 40 of the light transmitting member 30 on the housing surface 22. The surface of the cover member 20 functions as the pressing force suppression unit 60. That is, the surface of the cover member 20 is molded in a bank shape, whereby the pressing force suppression unit 60 is formed. As shown in FIG. 4, a pressing force suppression surface of the pressing force suppression unit 60 is inclined so as to be lowered toward the second direction DR2 (a direction from the wrist toward the lower arm) from the position of the convex portion 40. That is, the height of a direction DRH orthogonal to the housing surface 22 is inclined so as to be lowered toward the second direction DR2.

In FIGS. 3 and 4, although the detection unit 130 or the convex portion 40 (detection window) is provided in the first region RG1 on the hand side (three o'clock direction) of the housing surface 22 (rear surface), this embodiment is not limited thereto. For example, the detection unit 130 or the convex portion 40 (detection window) may be provided in a central region (a region through which a center line CL passes) or the like of the housing surface 22, and the pressing force suppression unit 60 may be provided in the periphery of the detection unit 130 or the convex portion 40 (detection window).

As shown in FIG. 4, the detection unit 130 is provided below the convex portion 40 of the light transmitting member 30. The upward direction is the direction DRH, and the downward direction is the direction opposite to the direction DRH. In other words, the downward direction is the direction from the rear surface (the surface on the side which comes into contact with the subject) of the main body 300 of the biological information detection apparatus toward the front surface (the surface on the side which does not come into contact with the subject). In this embodiment, the pulse wave sensor is a sensor unit which is constituted by the light transmitting member 30, the detection unit 130, or the like.

The detection unit 130 has a light receiving unit 140 and a light emitting unit 150. The light receiving unit 140 and the light emitting unit 150 are mounted on a substrate 160. The light receiving unit 140 receives light (reflected light, transmitted light, or the like) from the subject. The light emitting unit 150 emits light to the subject. For example, if the light emitting unit 150 emits light to the subject, and light is reflected by the subject (blood vessel), the light receiving unit 140 receives and detects the reflected light. The light receiving unit 140 can be realized by, for example, a light receiving element, such as a photodiode. The light emitting unit 150 can be realized by a light emitting element, such as an LED. For example, the light receiving unit 140 can be realized by a PN junction diode element formed on a semiconductor substrate. In this case, an angle limiting filter for narrowing a light receiving angle or a wavelength limiting filter for limiting the wavelength of light entering the light receiving element may be formed the diode element.

In the case of a pulsimeter as an example, light from the light emitting unit 150 travels inside the subject, and is diffused or scattered by an epidermis, a corium, a subcutaneous tissue, and the like. Thereafter, light reaches the blood vessel (a region to be detected) and is reflected. At this time, a part of light is absorbed by the blood vessel. Since the absorption rate of light in the blood vessel changes due to the effect of a pulse, and the amount of reflected light also changes, the light receiving unit 140 receives the reflected light to detect change in the amount of light, thereby detecting a pulse rate or the like as biological information.

In FIG. 4, although both the light receiving unit 140 and the light emitting unit 150 are provided as the detection unit 130, for example, only the light receiving unit 140 may be provided. In this case, for example, the light receiving unit 140 receives transmitted light from the subject. For example, when light from the light emitting unit 150 provided on the rear side of the subject transmits through the subject, the light receiving unit 140 receives and detects transmitted light.

In this embodiment, as shown in FIG. 4, diaphragm units 80 and 82 are provided. When the light receiving unit 140 is provided as the detection unit 130, the diaphragm units 80 and 82 narrow light from the subject in an optical path between the subject and the detection unit 130. When the light emitting unit 150 is provided as the detection unit 130, the diaphragm units 80 and 82 narrow light from the light emitting unit 150 in the optical path between the subject and the detection unit 130. In FIG. 4, the diaphragm units 80 and 82 are provided between the light transmitting member 30 and the detection unit 130. However, the diaphragm units 80 and 82 may be provided between the light transmitting member 30 and the subject or inside the light transmitting member 30. For example, the diaphragm units 80 and 82 are arranged near the light transmitting member 30.

In FIG. 4, a light shielding unit 100 is provided between the light receiving unit 140 and the light emitting unit 150. When both the light receiving unit 140 and the light emitting unit 150 are provided as the detection unit 130, for example, the light shielding unit 100 shields light from the light emitting unit 150 to suppress the direct entrance to the light receiving unit 140.

Figure 5A:
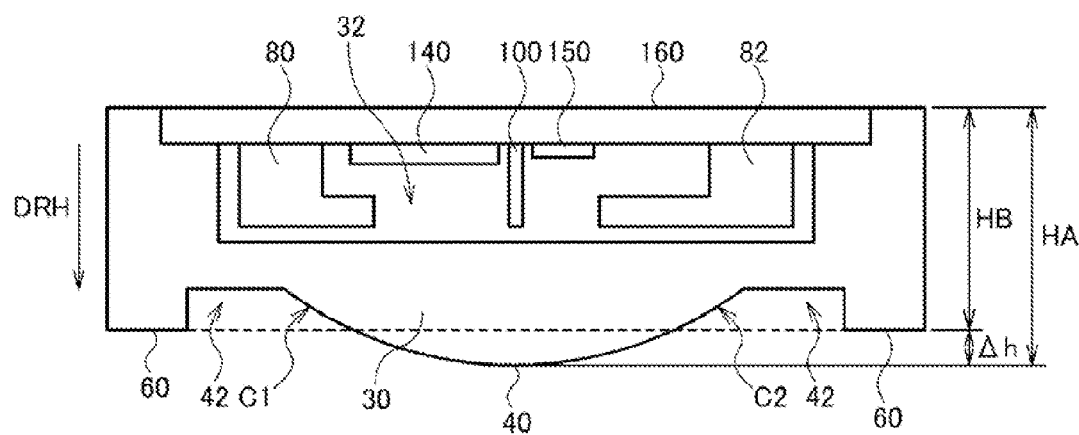
FIGS. 5A and 5B are explanatory views of a convex portion of a light transmitting member and a pressing force suppression unit.

2. Convex Portion of Light Transmitting Member and Pressing Force Suppression Unit As shown in FIG. 5A, in this embodiment, the light transmitting member 30 has the convex portion 40 which comes into contact with the subject to give the pressing force when measuring the biological information of the subject. The biological information detection apparatus has the pressing force suppression unit 60. The pressing force suppression unit 60 is disposed in periphery of the convex portion 40 on or above the housing surface (the surface on the subject side) of the biological information detection apparatus, and suppresses the pressing force given to the subject by the convex portion 40.

In this embodiment, for example, when the height of the convex portion 40 in the direction DRH orthogonal to the housing surface of the biological information detection apparatus is referred to as HA (for example, the height of the vertex of the curved shape of the convex portion 40), the height of the pressing force suppression unit 60 is referred to as HB (the height at the highest location), and the value (the difference between the heights HA and HB) obtained by subtracting the height HB from the height HA is referred to as $\Delta h$, the relationship of $\Delta h=HA-HB>0$ is established. For example, the convex portion 40 protrudes from the pressing force suppression surface of the pressing force suppression unit 60 toward the subject such that $\Delta h>0$. That is, the convex portion 40 protrudes toward the subject by the amount corresponding to $\Delta h$ from the pressing force suppression surface of the pressing force suppression unit 60.

In this way, the convex portion 40 having the relationship of $\Delta h>0$ is provided, making it possible to give an initial pressing force for exceeding, for example, a vein vanishing point to the subject. The pressing force suppression unit 60 for suppressing the pressing force given to the subject by the convex portion 40 is provided, making it possible to minimize change in pressing force in the use range in which the biological information is measured by the biological information detection apparatus, and to achieve reduction in noise component or the like. If the convex portion 40 protrudes from the pressing force suppression surface such that $\Delta h>0$, after the convex portion 40 comes into contact with the subject to give the initial pressing force, the pressing force suppression surface of the pressing force suppression unit 60 comes into contact with the subject, thereby suppressing the pressing force given to the subject by the convex portion 40. The vein vanishing point is a point which, when the convex portion 40 is brought into contact with the subject and the pressing force gradually increases, a signal due to a vein superimposed on a pulse wave signal is vanished or becomes small without affecting pulse wave measurement.

Figure 5B:
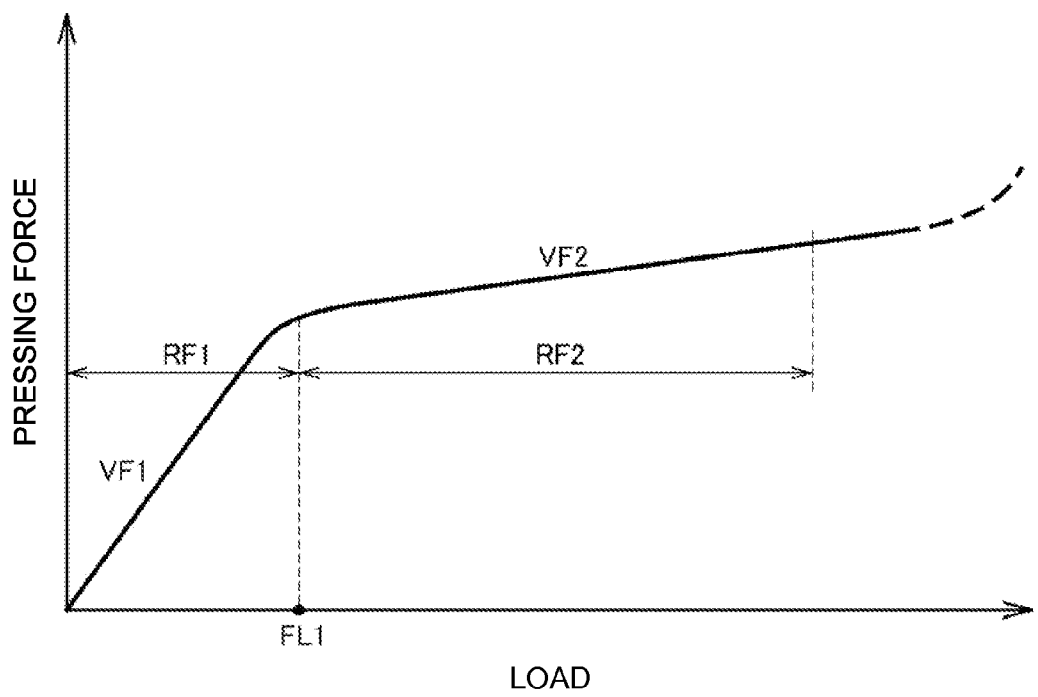

For example, in FIG. 5B, the horizontal axis represents a load which is generated by a load mechanism (a mechanism having an elastic member, such as spring or an extension/contraction portion, or a band) described referring to FIGS. 1B to 2C, and the vertical axis represents a pressing force (a pressure which is applied to a blood vessel) is given to the subject by the convex portion 40. The amount of change in pressing force of the convex portion 40 with respect to the load by the load mechanism generating the pressing force of the convex portion 40 is referred to as the amount of change in pressing force. The amount of change in pressing force corresponds to a slope of the characteristic of change in pressing force with respect to the load.

In this case, the pressing force suppression unit 60 suppresses the pressing force given to the subject by the convex portion 40 such that the amount VF2 of change in pressing force in a second load range RF2 in which the load of the load mechanism is greater than FL1 becomes smaller than the amount VF1 of change in pressing force in a first load range RF1 in which the load of the load mechanism becomes 0 to FL1. That is, in the first load range RF1 as an initial pressing force range, the amount VF1 of change in pressing force increases, and in the second load range RF2 as the use range of the biological information detection apparatus, the amount VF2 of change in pressing force decreases.

That is, in the first load range RF1, the amount VF1 of change in pressing force increases, thereby increasing the slope of the characteristic of change in pressing force with respect to the load. The pressing force having a large slope of the change characteristic is realized by Δh corresponding to the amount of protrusion of the convex portion 40. That is, the convex portion 40 having the relationship of Δh>0 is provided, whereby, even when the load by the load mechanism is small, it becomes possible to give the initial pressing force necessary for exceeding the vein vanishing point to the subject.

In the second load range RF2, since the amount VF2 of change in pressing force is small, it is possible to decrease the slope of the characteristic of change in pressing force with respect to the load. The pressing force having a small slope of the change characteristic is realized by pressing force suppression by the pressing force suppression unit 60. That is, the pressing force given to the subject by the convex portion 40 is suppressed by the pressing force suppression unit 60, whereby, in the use range of the biological information detection apparatus, even when there is change in load or the like, it becomes possible to minimize change in pressing force. Therefore, reduction in the noise component or the like is achieved.

In this way, an optimum pressing force (for example, about 16 kPa) is given to the subject, making it possible to obtain a pulse wave detection signal having a higher M/N ratio (S/N ratio). That is, it is possible to increase a signal component of the pulse wave sensor and to reduce a noise component. Here, M represents a signal level of the pulse wave detection signal, and N represents a noise level.

The range of the pressing force for pulse wave measurement is set to a range corresponding to the second load range RF2, making it possible to minimize change in pressing force (for example, about ±4 kPa) and to reduce the noise component.

The pressing force suppression unit 60 has the pressing force suppression surface which expands outward from around the convex portion 40. For example, the pressing force suppression unit 60 has the pressing force suppression surface which extends in the second direction DR2 orthogonal to the first direction DR1 as a circumferential direction of a region (wrist, arm, or the like) to be detected in plan view from a direction orthogonal to the housing surface. Specifically, as shown in FIGS. 3 and 4, the pressing force suppression unit 60 has the pressing force suppression surface which expands from the position of the convex portion 40 toward the second direction DR2 (the direction from the hand toward the lower arm). For example, the pressing force suppression surface of the pressing force suppression unit 60 is realized by a portion in a bank shape formed in the cover member 20.

In FIG. 3, a direction orthogonal to the first direction DR1 is referred to as the second direction DR2, and a direction opposite to the second direction DR2 is referred to as a third direction DR3. In this case, the pressing force suppression surface of the pressing force suppression unit 60 becomes a continuous surface in at least the first direction DR1, the second direction DR2, and the third direction DR3 around the convex portion 40. That is, the surface is continuous in at least three directions from the position of the convex portion 40. Specifically, as shown in FIG. 3, the pressing force suppression surface of the pressing force suppression unit 60 becomes a surface which is continuous over the entire circumference (four directions) of the convex portion 40. That is, the pressing force suppression surface is formed on the entire circumference of the convex portion 40. With this configuration, since it becomes possible to suppress the pressing force of the convex portion 40 by the pressing force suppression surface in at least the first, second, and third directions DR1, DR2, and DR3, it becomes possible to suppress the pressing force equally and efficiently.

In FIGS. 3 and 4, the light transmitting member 30 having the convex portion 40 is fixed to the housing surface 22. That is, since the light transmitting member 30 is fixed and attached to the housing surface 22, even when the load is applied to the load mechanism, the light transmitting member 30 does not relatively move with respect to the housing surface 22 (biological information detection apparatus). For example, when a damper mechanism is provided, and the load is applied by the load mechanism, while a movable structure in which the light transmitting member 30 moves vertically may be used, in FIGS. 3 and 4, this movable structure is not used.

In FIGS. 3 and 4, the pressing force suppression unit 60 is formed by an insulating member. That is, the pressing force suppression unit 60 is formed by an insulating member formed of an insulating material, such as resin (plastic), for suppressing the pressing force of the convex portion 40, instead of an electrode or the like formed by a conductive member (metal member) or the like.

In FIG. 5A, the diaphragm units 80 and 82 (aperture) or the light shielding unit 100 is provided, thereby reducing optical noise and further reducing the noise component on the pulse wave detection signal. For example, as indicated by C1 and C2, the diaphragm units 80 and 82 shield light passing through the marginal region of the convex portion 40. With this configuration, it is possible to suppress degradation in reliability of measured data or the like due to stray light at a location where the contact state is unstable as indicated by C1 and C2.

As the distance between the light receiving unit 140 and the light emitting unit 150 decrease, optical efficiency or performance is improved. However, if the distance between the light receiving unit 140 and the light emitting unit 150 decreases, there is an increasing possibility that direct light from the light emitting unit 150 enters the light receiving unit 140 and performance is deteriorated. Accordingly, in FIG. 5A, the light shielding unit 100 is provided between the light receiving unit 140 and the light emitting unit 150 to suppress the entrance of direct light from the light emitting unit 150 to the light receiving unit 140. With this, since it is possible to suppress superimposition of the noise component by direct light, it is possible to further improve the M/N ratio. A modification in which at least one of the diaphragm units 80 and 82 and the light shielding unit 100 is not provided may be made.

FIGS. 6A to 7B are diagrams illustrating a method of suppressing a pressing force by the pressing force suppression unit 60 in more detail.

Figure 6B:
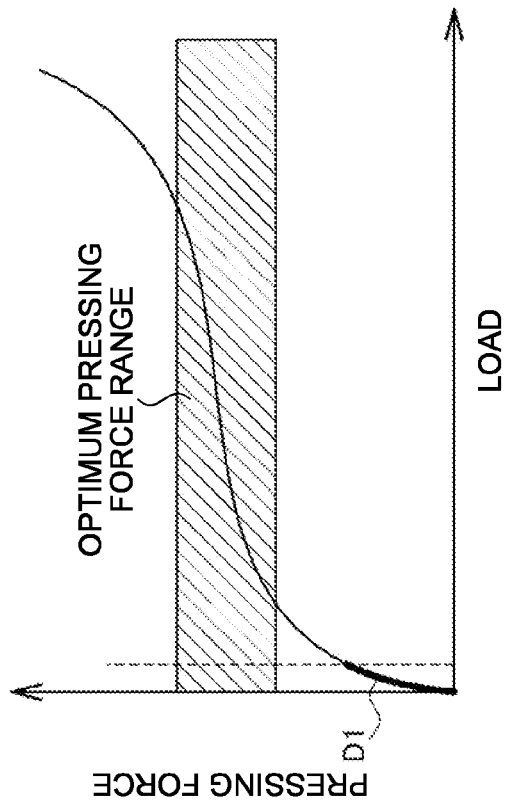
FIGS. 6A and 6B are explanatory views of a method of suppressing a pressing force by the pressing force suppression unit.
Figure 6A:
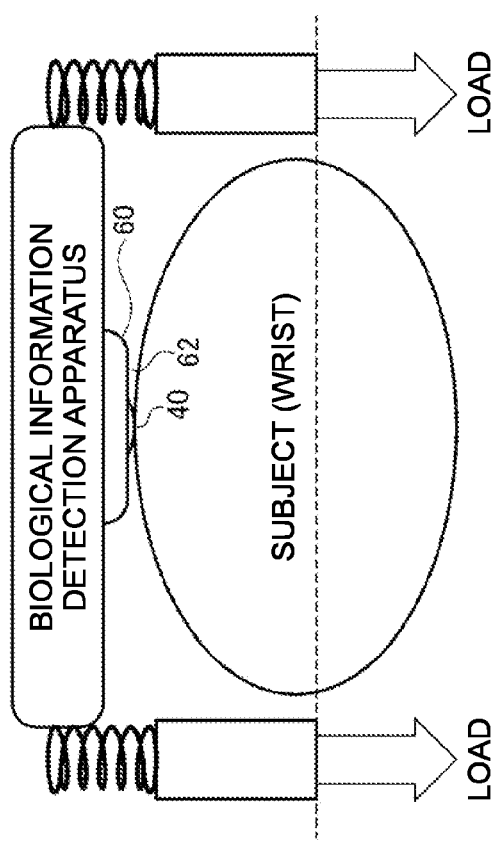

For example, in FIG. 6A, the convex portion 40 of the biological information detection apparatus comes into contact with the subject (wrist or the like). A pressing force suppression surface 62 of the pressing force suppression unit 60 does not come into contact with the subject.

As in FIG. 6A, if the convex portion 40 comes into contact with the surface (skin or the like) of the subject while the load is applied by the load mechanism, the convex portion 40 sinks into the surface, and as indicated by D1 of FIG. 6B, the pressing force increases quickly. This corresponds to the initial pressing force range described referring to FIG. 5B, and as described above, the amount of change in pressing force increases within the initial pressing force range. That is, since the convex portion 40 is provided, even when the load by the load mechanism is small, it becomes possible to give the initial pressing force necessary for exceeding the vein vanishing point to the subject.

Figure 7B:
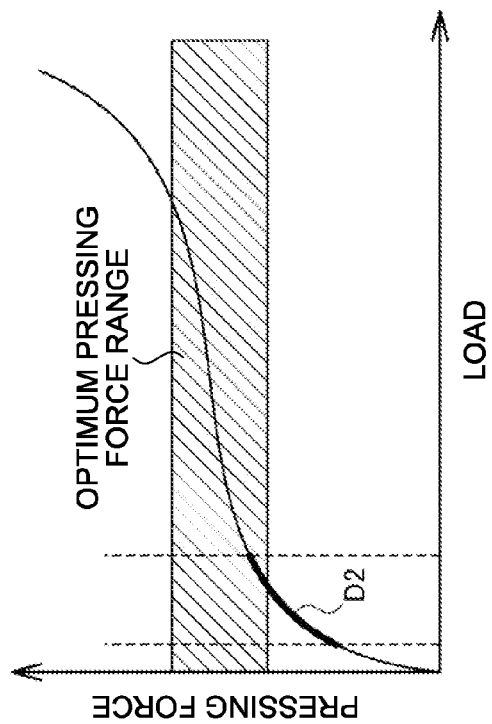
FIGS. 7A and 7B are explanatory views of the method of suppressing a pressing force by the pressing force suppression unit.
Figure 7A:
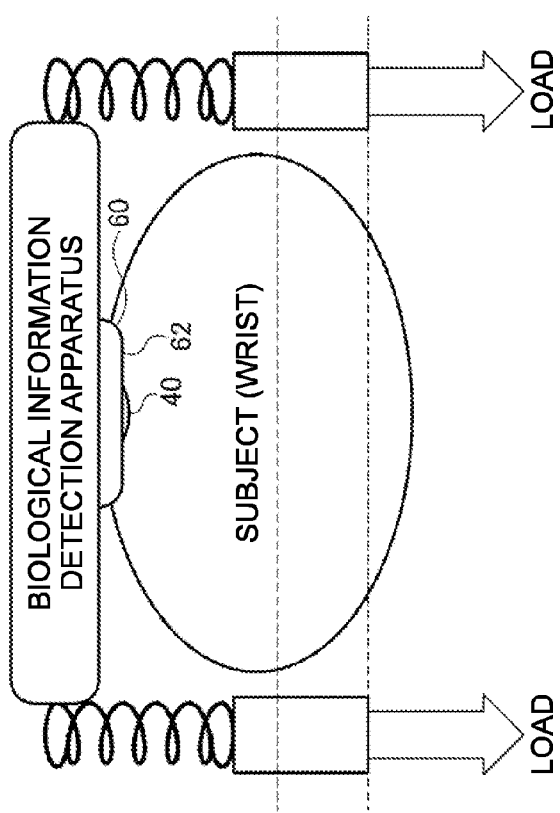

In FIG. 7A, the load by the load mechanism further increases, whereby the pressing force suppression surface 62 of the pressing force suppression unit 60 as well as the convex portion 40 comes into contact with the surface (skin or the like) of the subject. In this way, the pressing force suppression surface 62 comes into contact with the surface of the subject, whereby the contact area with the subject increases. Accordingly, as indicated by D2 of FIG. 7B, an increase in pressing force given to the subject by the convex portion 40 is suppressed. That is, the amount of change in pressing force described referring to FIG. 5B decreases as indicated by D2 of FIG. 7B. That is, a slope of the characteristic of change in pressing force with respect to the load decreases. Accordingly, even if the load by the load mechanism increases, the degree of increase in pressing force (pressure per unit area) given to the subject by the contact surface of the convex portion 40 is weakened. Accordingly, in the optimum pressing force range (RF2 of FIG. 5B), it becomes possible to sufficiently decrease the amount of change in pressing force (the slope of the characteristic of change). Therefore, in the use range of the biological information detection apparatus, even when there is change in load or the like, it becomes possible to minimize change in pressing force and to improve the MN ratio representing signal quality.

In this way, in this embodiment, the convex portion 40 having the relationship of Δh>0 is provided, whereby, in the initial pressing force range, the pressing force given to the subject by the convex portion 40 increases quickly. The pressing force suppression unit 60 (pressing force suppression surface) is provided around the convex portion 40, whereby, in the use range, with pressing force suppression by the pressing force suppression unit 60, the amount of change in pressing force which is the amount of change in pressing force with respect to the load decreases to reduce change in pressing force.

3. Δh of Convex Portion

Δh which represents the amount of protrusion of the convex portion 40 is an important parameter which specifies an optimum pressing force. That is, in order to constantly give the pressing force for exceeding the vein vanishing point, a certain amount of protrusion is required, and Δh should be set to a large value. However, if Δh becomes an excessive value, this may cause a decrease in the signal component of the pulse wave sensor or an increase in change in pressing force.

Accordingly, the minimum Δh is selected in a range in which the signal component of the pulse wave sensor can be sufficiently ensured, that is, in a range in which the optimum pressing force can be given. That is, in the range in which the optimum pressing force can be given, the smaller Δh, the lower the noise component can be suppressed.

Figure 8A:
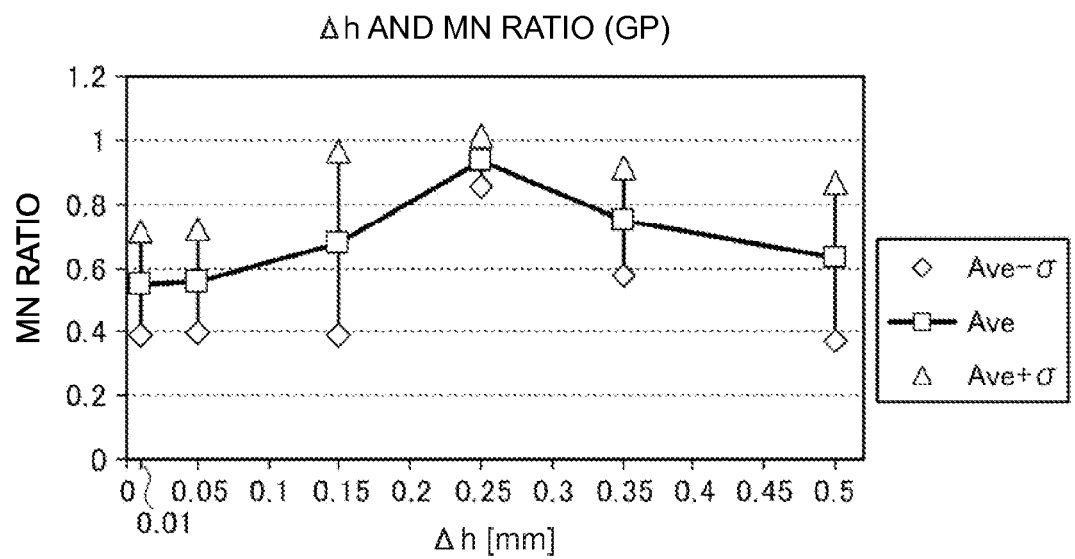
FIGS. 8A and 8B are diagrams showing the relationship between Δh and an MN ratio.
Figure 8B:
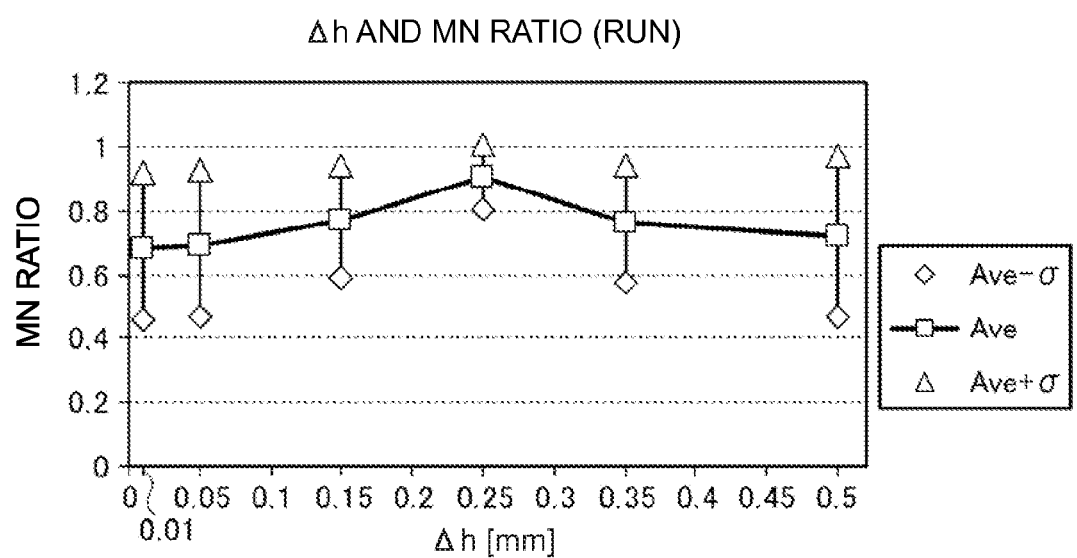

For example, FIG. 8A shows an example of a measured value which represents the relationship between Δh and the MN ratio (SN ratio) when the user performs a clasp and unclasp operation (GP). FIG. 8B shows an example of a measured value which represents the relationship between Δh and the MN ratio when the user performs a run operation (RUN). Here, the MN ratio corresponds to the ratio of the signal component (M) of the pulse wave sensor and the noise component (N).

For example, in FIGS. 8A and 8B, as Δh increases from 0.01 mm to 0.05 mm, the MN ratio tends to increase. Furthermore, as Δh increases from 0.05 mm to 0.15 mm and from 0.15 mm to 0.25 mm, the MN ratio tends to increase. The rate of increase of the MN ratio in the range of 0.05 mm to 0.25 mm tends to be higher than the rate of increase in the range of 0.01 mm to 0.05 mm. The rate of increase of the MN ratio in the range of 0.15 mm to 0.25 mm tends to be higher than the rate of increase in the range of 0.05 mm to 0.15 mm.

As Δh decreases from 0.5 mm to 0.35 mm, the MN ratio tends to increase. As Δh decreases from 0.35 mm to 0.25 mm, the MN ratio tends to increase. The rate of increase of the MN ratio in the range of 0.35 mm to 0.25 mm tends to be higher than the rate of increase in the range of 0.5 mm to 0.35 mm.

From above, the range of Δh is preferably 0.01 mm $\leq$ Δh $\leq$ 0.5 mm, and more preferably, 0.05 mm $\leq$ Δh $\leq$ 0.35 mm. For example, when Δh=about 0.25 mm, it becomes possible to maximize the MN ratio. That is, in this way, Δh is set to a small value, whereby an increase in the noise component due to change in pressing force or the like is suppressed while giving the minimum pressing force for exceeding the vein vanishing point to the subject, making it possible to increase the MN ratio representing signal quality.

In this embodiment, the convex portion 40 has a curved shape in at least a portion in contact with the subject. In this way, if the surface shape of the convex portion 40 is a curved shape, it becomes possible to give the pressing force to the subject by the convex portion in a stable contact state.

In this case, if the radius of curvature of the curved shape of the convex portion is R, for example, it is preferable that R$\geq$8 mm. With this, it becomes possible to efficiently give the pressing force under a condition of a radius of curvature at which the contact state with the surface of a living body, such as hide, is stable.

4. Groove Portion

As shown in FIG. 5A, in this embodiment, a groove portion 42 is provided between the convex portion 40 of the light transmitting member 30 and the pressing force suppression unit 60.

Figure 9A:
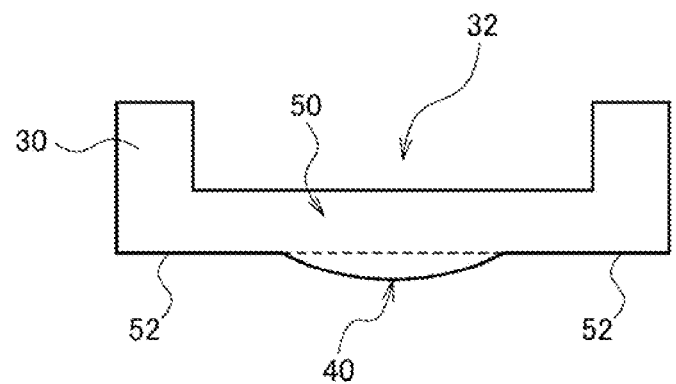
FIGS. 9A and 9B are explanatory views of a problem due to change in a contact state around the convex portion.

In contrast, in the light transmitting member 30 of FIG. 9A, the groove portion 42 as shown in FIG. 5A is not provided, and only a flat portion 52 is provided. For example, the height of the flat portion 52 becomes equal to the height of the pressing force suppression unit 60 (the height in the end portion).

However, as in FIG. 9A, if a configuration in which the groove portion 42 is not provided is made, it has been found that there are the following problems.

Figure 9B:
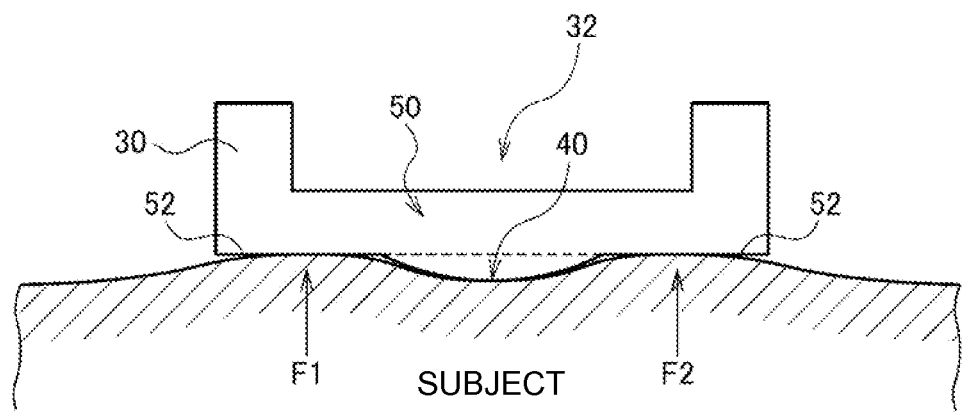

For example, FIG. 9B shows a state where the light transmitting member 30 of FIG. 9A is in contact with the subject. As shown in FIG. 9B, if the surface of a relatively soft subject, such as skin, comes into contact with the contact surface of the light transmitting member 30 formed of a hard material, such as resin or glass, the contact state becomes unstable. For example, in F1 and F2 of FIG. 9B, the flat portion 52 of the light transmitting member 30 and the surface (skin) of the subject are in a weak contact state. In this case, for example, the surface of the subject is separated from the flat portion 52 of the light transmitting member 30 over time or the like to cause a non-contact state or the like, and the contact state dynamically changes. Then, light intensity is likely to be optically generated due to dynamic change in a contact state, and if light enters the light receiving unit 140, light becomes noise having no correlation with a pulse component.

For example, in order to obtain a pulse wave detection signal with a low noise component, it is possible to give the initial pressing force for exceeding the vein vanishing point to the surface of the subject. In FIG. 9B, while a sufficient appropriate pressing force for exceeding the vein vanishing point is given to the contact surface of the convex portion 40, an appropriate pressing force is not given to the contact surface in a weak contact state indicated by F1 and F2. Accordingly if light from the contact surface of F1 and F2 enters the light receiving unit 140 of FIG. 5A, there is a situation in which noise having no correlation with a pulse component is superimposed on the pulse wave detection signal. That is, since the pulse wave detection signal is detected by the total amount of received light by the light receiving unit 140, in addition to light from the contact surface of the convex portion 40, if light from the contact surface in a weak contact state of F1 and F2 enters the light receiving unit 140, a component of light acts as a noise component, causing a decrease in the MN ratio of the pulse wave detection signal.

Figure 10A:
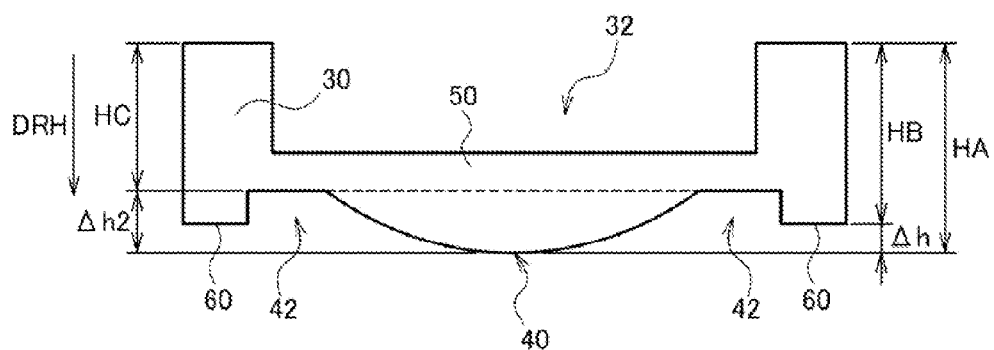
FIGS. 10A and 10B are explanatory views of a method of this embodiment in which a groove portion is provided.

Accordingly, in order to suppress adverse effects due to dynamic change in a contact state around the convex portion 40, in this embodiment, as shown in FIG. 10A, the groove portion 42 is provided between the convex portion 40 of the light transmitting member 30 and the pressing force suppression unit 60. That is, the pressing force suppression unit 60 in a bank shape lower than the convex portion 40 is provided around the convex portion 40 which constitutes a pulse wave sensor, and the groove portion 42 which becomes a gap is provided between the convex portion 40 and the pressing force suppression unit 60. For example, the bottom surface of the groove portion 42 is constituted by the surface (the surface on the subject side) of the light transmitting member 30.

Figure 10B:
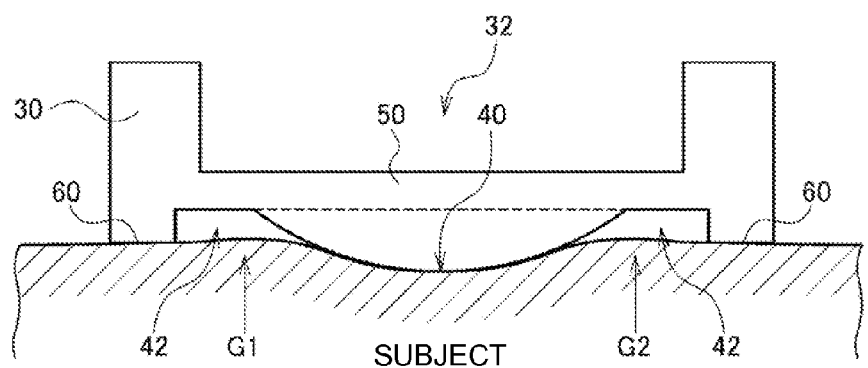

With this configuration, as indicated by G1 and G2 of FIG. 10B, it is possible to suppress dynamic change in a contact state around the convex portion 40. That is, it is possible to effectively suppress the periphery (flat portion) of the convex portion 40 and the surface of the subject from being in an unstable contact state as indicated by F1 and F2 of FIG. 9B. That is, since the bottom surface of the convex portion 42 indicated by G1 and G2 of FIG. 10B is in a non-contact with the subject, dynamic change in a contact state is less likely to be generated.

Figure 23B:
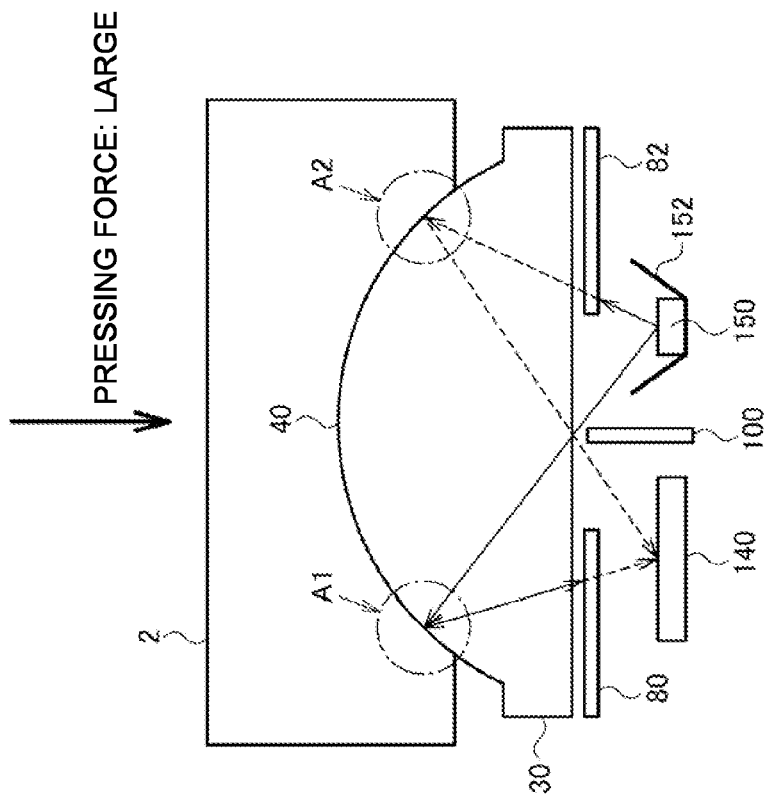
FIGS. 23A and 23B are explanatory views of a method of providing a diaphragm unit or a light shielding unit.
Figure 23A:
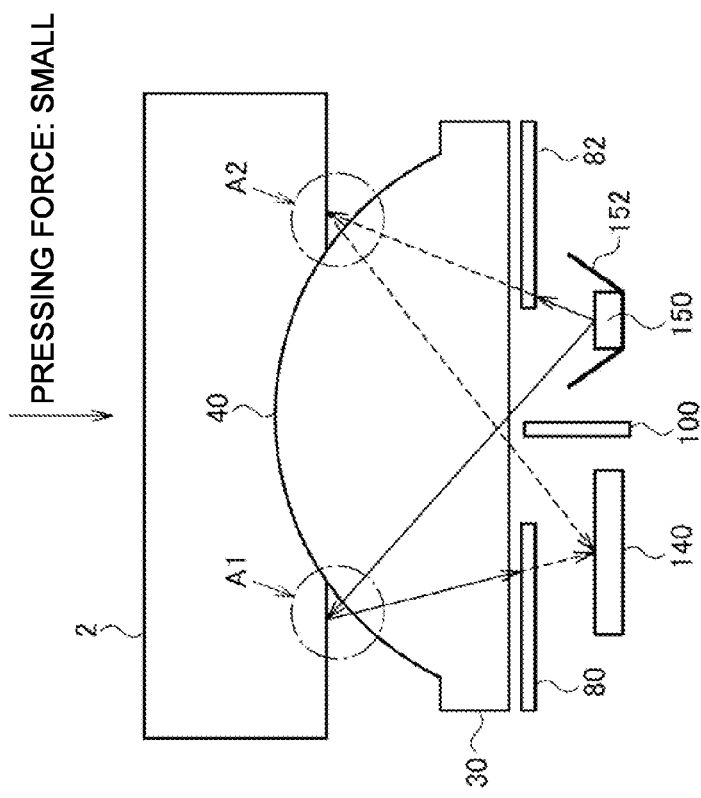

For example, if the diaphragm units 80 and 82 and the like as shown in FIGS. 23A and 23B are provided such that light in G1 and G2 of FIG. 10B does not enter the light receiving unit 140, it is possible to effectively suppress a decrease in the MN ratio of the pulse wave detection signal due to stray light in G1 and G2.

In this case, in a method in which the groove portion 42 is not provided, in order to suppress adverse effects due to stray light, it is necessary to further decrease the opening area of the diaphragm units 80 and 82. If the opening area of the diaphragm units 80 and 82 decreases, the amount of received light of the light receiving unit 140 decrease, the signal component of the pulse wave detection signal decreases, and the MN ratio decreases. In this reason, as in this embodiment, if the groove portion 42 is provided, it becomes possible to increase the opening area of the diaphragm units 80 and 82 to some extent, and to suppress a decrease in the MN ratio.

In order to obtain the pressing force as indicated by D1 of FIG. 6B, it is necessary to cause the load to concentrate on the convex portion 40 at the time of the initial pressing force. In this regard, if the groove portion 42 as in this embodiment is provided, it is possible to suppress a situation in which the surface around the convex portion 40 comes into contact with the surface of the subject at the time of the initial pressing force and the load is dispersed to the convex portion 40. Accordingly, it becomes possible to cause the load to concentrate on the convex portion 40 at the time of the initial pressing force, and it becomes easy to give an appropriate pressing force for exceeding the vein vanishing point to the surface of the subject.

In this embodiment, for example, as shown in FIG. 4, the groove portion 42 is provided over the entire circumference of the convex portion 40. That is, the sectional shape of the groove portion 42 is a groove shape (concave shape) in the entire section passing through the position of the convex portion 40. In this way, it becomes possible to suppress the occurrence of dynamic change in a contact state on the entire circumference of the convex portion 40, and to realize stable improvement of signal quality of a detection signal.

However, this embodiment is not limited thereto, and for example, it should suffice that the groove portion 42 has a groove shape (concave shape) in a predetermined section as shown in FIG. 10A. Specifically, it should suffice that the groove portion 42 has a groove shape (concave shape) in the section (the surface orthogonal to the housing surface) in at least three directions (first, second, and third directions DR1, DR2, and DR3). For example, there may be a region where the groove portion 42 is not formed in a portion of the periphery of the convex portion 40. For example, a connecting member (bridge) or the like which connects the convex portion 40 and the pressing force suppression unit 60 may be provided in a portion of the periphery of the convex portion 40.

As shown in FIG. 10A, the height of the convex portion 40 in the direction DRH orthogonal to the housing surface 22 of the biological information detection apparatus, the height of the pressing force suppression unit 60, and the height of the bottom surface of the groove portion 42 are respectively referred to as HA, HB, and HC. For example, when the convex portion 40 has a curved shape, HA is the height of the vertex of the curved surface. HB is, for example, the height at the highest location of the pressing force suppression unit 60. HC is the height of a plane which forms at least a part of the bottom surface of the groove portion 40.

In this case, in this embodiment, the relationship of HA>HB>HC is established. That is, the convex portion 40 is the highest, the pressing force suppression unit 60 is the second highest, and the bottom surface of the groove portion 42 is the lowest.

With this configuration, when the load is applied by the load mechanism, the convex portion 40 first comes into contact with the surface of the subject, and the initial pressing force is obtained accordingly. Thereafter, the pressing force suppression unit 60 comes into contact with the surface of the subject, whereby the pressing force suppression effect described by D2 of FIG. 7B is obtained. In this way, even when the convex portion 40 and the pressing force suppression unit 60 come into contact with the subject of the subject, as indicated by G1 and G2 of FIG. 10B, the surface of the subject does not come into contact with the bottom surface of the groove portion 42 having low height. Accordingly, it becomes possible to effectively suppress a decrease in the MN ratio or the like when the contact state becomes unstable.

The depth of the groove portion 42 is set such that the bottom surface does not come into contact with the surface (skin) of the subject when the load is applied by the load mechanism. For example, as shown in FIG. 10A, when the difference between the height HA of the convex portion 40 and the height HC of the bottom surface of the groove portion 42 is $\Delta h2 = HA - HC$, in this embodiment, it is preferable that $\Delta h2 > 0.5$ mm.

Figure 11:
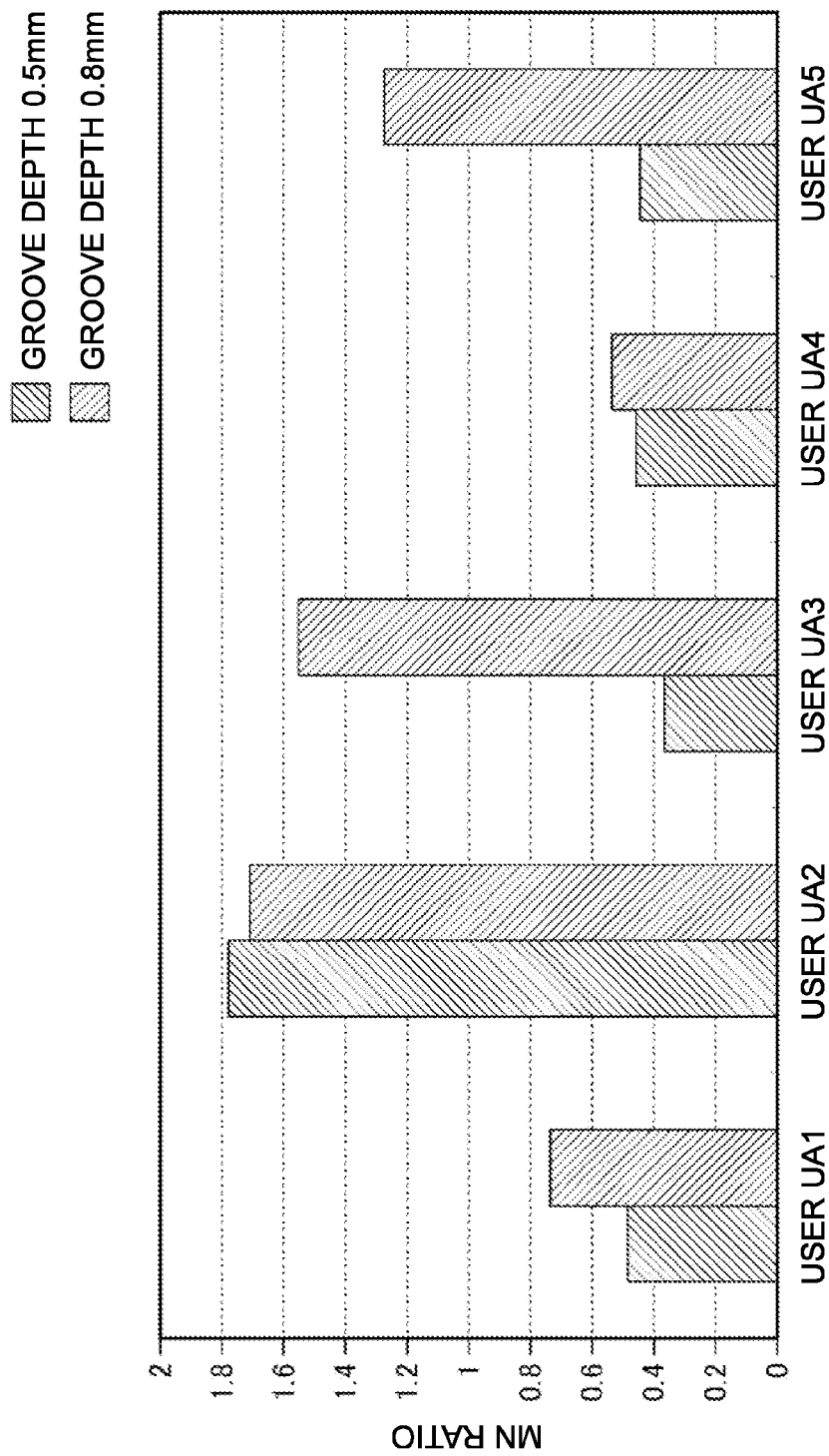
FIG. 11 is a diagram showing the relationship between the depth of a groove portion and an MN ratio.

For example, FIG. 11 shows an example of a measured value which represents the relationship between the depth of the groove portion 42 and the MN ratio. The depth of the groove portion 42 corresponds to Δh2. As shown in FIG. 11, for many users, the MN ratio of the pulse wave detection signal becomes higher when the depth of the groove portion 42 is 0.8 mm than when the depth of the groove portions 42 is 0.5 mm. If the depth (Δh2) of the groove portion 42 becomes equal to or smaller than 0.5 mm, for many users, the MN ratio of the pulse wave detection signal decreases quickly. For example, for a user who has comparatively soft skin elasticity, even if the groove portion 42 is provided, if the depth is shallow, the bottom surface of the groove portion 42 and the surface of skin are in a contact state (weak contact state) in G1 and G2 of FIG. 10B, and the MN ratio is deteriorated due to stray light or the like in this portion. From this, it is preferable that Δh2 corresponding to the depth of the groove portion 42 is greater than 0.5 mm.

In FIG. 3, while the groove portion 42 has a concentrically circular shape with respect to the convex portion 40, the shape of the groove portion 42 of this embodiment is not limited thereto, and various modifications may be made. For example, as the shape of the groove portion 42, various shapes, such as a shape in which the convex portion 40 and the pressing force suppression unit 60 are connected by a connecting member in a portion of the periphery of the convex portion 40, may be used.

Processing for light shielding may be performed on the inner wall, the bottom surface, or the like of the groove portion 42. For example, the color of the inner wall or the bottom surface of the groove portion 42 has a predetermined color, such as black. Alternatively, processing for roughening the surface of the inner wall or the bottom surface of the groove portion 42 to suppress reflectance of light, or the surface of the inner wall or the bottom surface of the groove portion 42 has a moth eye structure, thereby forming an anti-reflection structure. With this, it is possible to suppress a situation in which reflected light in the groove portion 42 becomes stray light and then a noise component of measured data.

5. Details of Pressing Force Suppression Unit

Next, a detailed example of the pressing force suppression unit 60 will be described. In the pressing force suppression unit 60 (bank structure), the area (the contact area with the subject) of the pressing force suppression surface 62 increases, thereby suppressing change in pressing force (contact pressure) applied near the convex portion 40.

However, if the area of the pressing force suppression surface 62 is too large, and the height of the pressing force suppression surface 62 with respect to the pulse wave sensor is too high, there is a problem in that the pressing force applied near the convex portion 40 may not reach an appropriate range, and quality of the pulse wave detection signal may not be sufficient.

If the area of the pressing force suppression surface 62 is small or the height of the pressing force suppression surface 62 is low, there is a problem in that the pressing force suppression effect may not be sufficiently exhibited. When the pressing force suppression effect may not be exhibited, this means that change in pressing force increases and the noise component of the pulse wave detection signal increases.

Figure 12A:
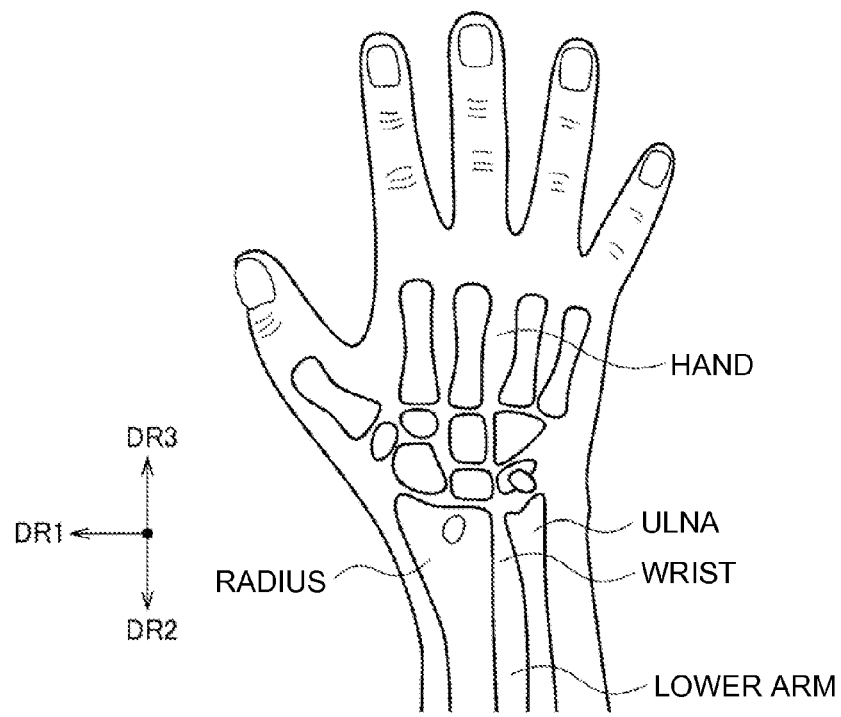
FIGS. 12A and 12B are explanatory views of a problem when putting the biological information detection apparatus on a wrist.
Figure 12B:
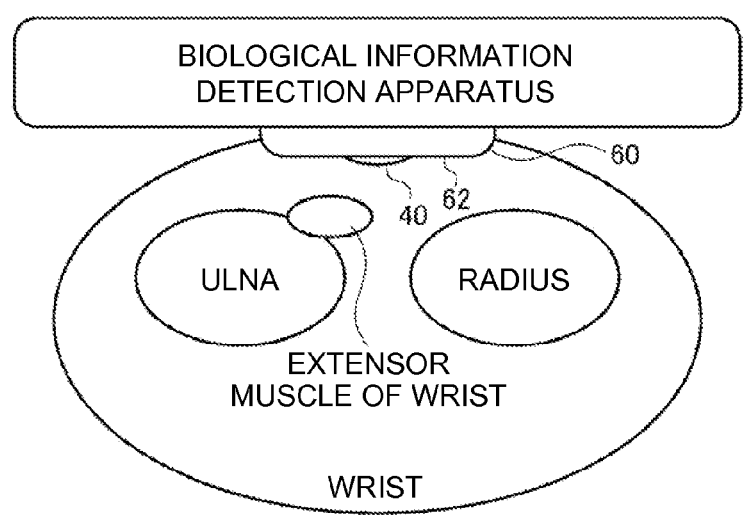

For example, as shown in FIG. 12A, as a bone near the wrist, there are the radius on the thumb side and the ulna on the little finger side. As shown in FIG. 12B, the convex portion 40 of the biological information detection apparatus or the pressing force suppression surface 62 of the pressing force suppression unit 60 comes into contact with the skin of the wrist, when detecting biological information, such as a pulse wave, it is desirable to increase the contact area of the pressing force suppression surface 62 and the skin of the wrist while suppressing the occurrence of interference with the radius or the ulna. With this, it becomes possible to allow the pressing force to be easily applied to the pulse wave sensor and to effectively suppress change in pressing force.

For this reason, in the biological information detection apparatus of this embodiment, the pressing force suppression unit 60 which suppresses the pressing force given to the subject by the convex portion 40 is provided.

Figure 13:
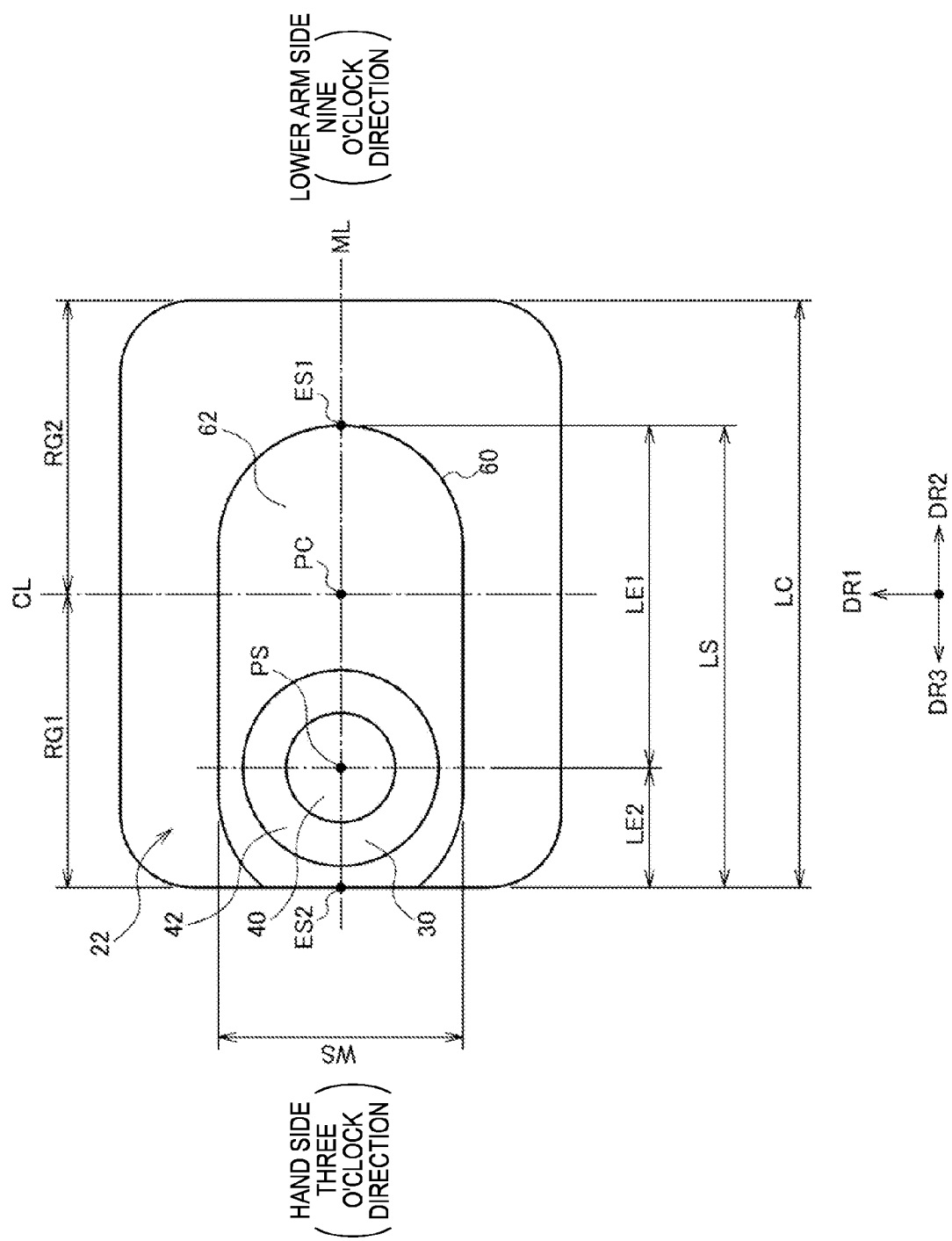
FIG. 13 is a top view illustrating the details of the pressing force suppression unit.

As shown in FIG. 13, when the housing surface 22 is divided into the first region RG1 and the second region RG2 by the center line CL in the first direction DR1, the convex portion 40 (pulse wave sensor) is provided in the first region RG1.

For example, a direction which is orthogonal to the first direction DR1 and from the convex portion 40 toward the center line CL is referred to as the second direction DR2. When the biological information detection apparatus is put on the wrist of the subject, the second direction DR2 becomes the direction from the hand of the subject toward the lower arm. At this time, the convex portion 40 is provided on the hand side out of the hand and the lower arm of the subject. That is, the convex portion 40 is provided in the first region RG1 on the hand side out of the first region RG1 on the hand side and the second region RG2 on the lower arm side.

Figure 14:
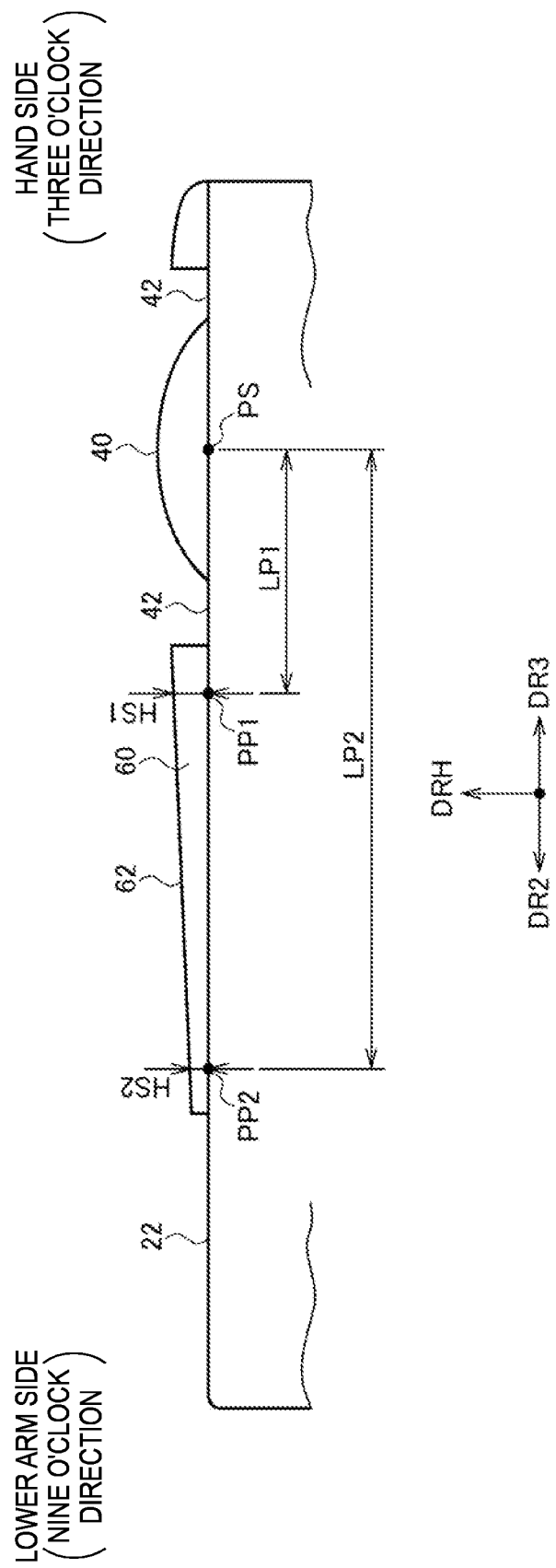
FIG. 14 is a sectional view illustrating the details of the pressing force suppression unit.

As shown in FIGS. 13 and 14, the pressing force suppression unit 60 has the pressing force suppression surface 62 which extends from the position PS of the convex portion 40 (the highest position of the convex portion) in the second direction DR2. That is, the pressing force suppression surface 62 expands from the position PS of the convex portion 40 toward the second direction DR2 (lower arm side).

Specifically, the pressing force suppression surface 62 is the surface which extends in the second direction DR2 from the position PS of the convex portion 40 beyond the center line CL. For example, as shown in FIG. 13, when the length of the pressing force suppression surface 62 (pressing force suppression unit) is referred to as LS, and the length of the housing surface 22 (the rear surface or the rear lid of the main body) is referred to as LC, LS<LC. In this case, for example, it is preferable that $(1/2) \times LC \leq LS \leq (3/4) \times LC$. That is, it is preferable that the position of a first end portion ES1 toward the second direction DR2 (nine o'clock side) of the pressing force suppression surface 62 is the position equal to or greater than half the case (rear lid), and the position equal to or smaller than ¾.

The lengths LS and LC are the length of the pressing force suppression surface 62 (pressing force suppression unit) in the second direction DR2 at the position PS of the convex portion 40. Specifically, when a line which is orthogonal to the center line CL and passes through the position PS of the convex portion 40 is referred to as ML, LS is the length of the pressing force suppression surface 62 on the line ML, and LC is the length of the housing surface 22 (rear lid) on the line ML.

A direction opposite to the second direction DR2 is referred to as the third direction DR3, the distance between the position PS of the convex portion 40 and the first end portion ES1 toward the second direction DR2 of the pressing force suppression surface 62 (pressing force suppression unit) is referred to as LE1, and the distance between the position PS of the convex portion 40 and a second end portion ES2 toward the third direction DR3 of the pressing force suppression surface 62 is referred to as LE2. In this case, in FIG. 13, LE1>LE2.

With this configuration, since LE2 is small, the convex portion 40 is arranged near the second end portion ES2 of the pressing force suppression surface 62. Since LE1 is large, it becomes possible to form the pressing force suppression surface 62 which expands over a long distance from the position of the convex portion 40 toward the first end portion ES 1.

When the width of the pressing force suppression surface 62 in the first direction DR1 at the position PS of the convex portion 40 is WS, WS<LE1.

With this configuration, the width WS of the pressing force suppression surface 62 in the first direction DR1 decreases, thereby forming the pressing force suppression surface 62 in which the first direction DR1 becomes the latitudinal direction and the second direction DR2 becomes the longitudinal direction.

The first and second end portions ES1 and ES2 are, for example, the end portions of the pressing force suppression surface 62 (pressing force suppression unit) on the line ML orthogonal to the center line CL. LE1 is the distance between the position PS of the convex portion 40 and the first end portion ES1 on the line ML, and LE2 is the distance between the position PS of the convex portion 40 and the second end portion ES2 on the line ML. WS is the width of the pressing force suppression surface 62 (pressing force suppression unit) on a line which passes through the position PS of the convex portion 40 and is parallel to the center line CL.

For example, the arm of a human has a tapered shape which increases in thickness from the hand side toward the elbow side, and the elbow side has greater change in diameter of the arm than the hand side.

In this regard, in this embodiment, as shown in FIG. 13, the convex portion 40 (pulse wave sensor) is provided in the first region RG1 which is the region on the hand side (the three o'clock direction when the biological information detection apparatus is put on the left hand). Accordingly, stability when the biological information detection apparatus is put on the wrist is excellent, and comfort is excellent. As described above, since the arm has a tapered shape, when the convex portion 40 is arranged in the first region RG1, change in diameter of the arm is small, and change in pressing force is small. As a result, noise which is superimposed on the pulse wave detection signal decreases, thereby improving the MN ratio.

As described referring to FIG. 5B, in the use range in which the biological information is measured by the biological information detection apparatus, it is desirable to decrease the slope in the characteristic of change in pressing force with respect to the load to minimize change in pressing force. For this reason, as indicated by D2 of FIG. 7B, the pressing force suppression unit 60 suppresses the pressing force given to the subject by the convex portion 40, thereby reducing pressing force concentration in the convex portion 40. In order to increase the pressing force suppression effect, it is necessary to make the area of the pressing force suppression surface 62 as the contact surface with a living body as large as possible.

In this case, if the contact area of the pressing force suppression surface 62 expands toward the first direction DR1 of FIG. 13, the width WS of the pressing force suppression surface 62 increases. However, as shown in FIGS. 12A and 12B, since there are the radius and the ulna near the wrist, if the width WS of the pressing force suppression surface 62 increases, the pressing force suppression surface 62 interferes with the radius, the ulna, or the like. If such interference occurs, the initial pressing force by the convex portion 40 as indicated by D1 of FIG. 6B is suppressed, and it is not possible to give the initial pressing force for exceeding the vein vanishing point to the subject.

Accordingly, in FIG. 13, the pressing force suppression surface 62 becomes the surface which extends (the surface which expands) toward the second direction DR2, and the contact area with the living body expands toward the second direction DR2. Specifically, the pressing force suppression surface 62 has a pseudo elliptical shape (track shape) in which the second direction DR2 is the major axis direction. That is, as described above, the relationship of LE1>LE2 is established between the distance LE1 between the position PS of the convex portion 40 and the first end portion ES1 and the distance LE2 between the position PS of the convex portion 40 and the second end portion ES2, and the relationship of WS<LE1 or WS<LE1+LE2 is established between the width WS of the pressing force suppression surface 62 and LE1 and LE2.

With this configuration, the width WS decreases to suppress interference between the pressing force suppression surface 62 and the radius or ulna, it becomes possible to sufficiently ensure the initial pressing force by the convex portion 40 (D1 of FIG. 6B). Also, the contact area of the pressing force suppression surface 62 expands toward the second direction DR2, it becomes possible to suppress the pressing force of the convex portion 40 (D2 of FIG. 7B), thereby minimizing change in pressing force in the use range. That is, it becomes possible to realize both ensuring of a sufficient initial pressing force by the convex portion 40 and suppression of change in pressing force in the use range, and to reduce the noise component to ensure a sufficient MN ratio.

In this case, if the length of the pressing force suppression surface 62 in the second direction DR2 is too long so as to ensure the contact area, motion of a muscle, a tendon, or the like, change in diameter of the arm, or the like at a position (for example, the first end portion ES 1 on the lower arm side) away from the convex portion 40 is transmitted to the portion of the convex portion 40 (pulse wave sensor). Accordingly, change in pressing force in the convex portion 40 occurs, and as a result, body motion noise is more greatly superimposed.

Accordingly, in FIG. 13, while the pressing force suppression surface 62 becomes the surface which extends in the second direction DR2 from the position of the convex portion 40 beyond the center line CL, the relationship of LS<LC is established between the length LS of the pressing force suppression surface 62 in the second direction DR2 and the length LC of the housing surface 22. More preferably, the relationship of $(1/2) \times LC \leq LS \leq (3/4) \times LC$ is established. In this way, if the length LS in the second direction DR2 of the pressing force suppression surface 62 is suppressed to a certain length, it is possible to effectively suppress a situation in which motion of a muscle, a tendon, or the like at a location away from the convex portion 40 is transmitted to the portion of the convex portion 40 and body motion noise is superimposed.

In this embodiment, as shown in FIG. 14, an extended portion toward the second direction DR2 of the pressing force suppression surface 62 is inclined with reference to the housing surface 22 (case bottom surface).

For example, in FIG. 14, a position away from the position PS of the convex portion 40 at a first distance LP1 in the second direction DR2 (broadly, a predetermined direction) is referred to as a first position PP1, and a position away from the position PS of the convex portion 40 at a second distance LP2 longer than the first distance LP1 in the second direction DR2 (predetermined direction) is referred to as a second position PP2. The first and second positions PP1 and PP2 are, for example, the positions on the line ML along the second direction DR2 (predetermined direction) in FIG. 13. The height of the pressing force suppression surface 62 in the direction DRH orthogonal to the housing surface 22 at the first position PP1 is referred to as HS1, and the height of the pressing force suppression surface 62 in the direction DRH at the second position PP2 is referred to as HS2. Then, in FIG. 14, the relationship of HS1>HS2 is established. Specifically, the pressing force suppression surface 62 is inclined such that the height in the direction DRH orthogonal to the housing surface 22 is lowered toward the second direction DR2 (predetermined direction) from the position PS of the convex portion 40. For example, the inclination is provided at an angle in a range of about 3 degrees to 6 degrees. As in FIG. 14, for example, various modifications may be made, in which an inclination is provided such that the height changes in a stepwise manner, instead of an inclination such that the height changes smoothly.

The inclination is provided, whereby, for example, it is possible to suppress pressing force concentration near the first end portion ES1 on the second direction DR2 side (nine o'clock side) of the pressing force suppression surface 62. Accordingly, the load is easily applied to the convex portion 40, and it becomes easy to obtain an appropriate pressing force. For example, as described above, the arm has a tapered shape. Accordingly, for example, if the first end portion ES1 on the second direction DR2 side is high, even if the bands 320 and 322 of FIGS. 1A and 1B are fastened tightly, and the load is applied to the convex portion 40, there is a strong tendency that the load is received in the first end portion ES 1. Accordingly, no matter how the bands 320 and 322 are fastened tightly, there is a problem in that it is not possible to apply a necessary load to the convex portion 40 (pulse wave sensor), and it becomes difficult to obtain an appropriate pressing force. In this regard, as in FIG. 14, if the pressing force suppression surface 62 is inclined, it is possible to solve this problem.

Figure 15:
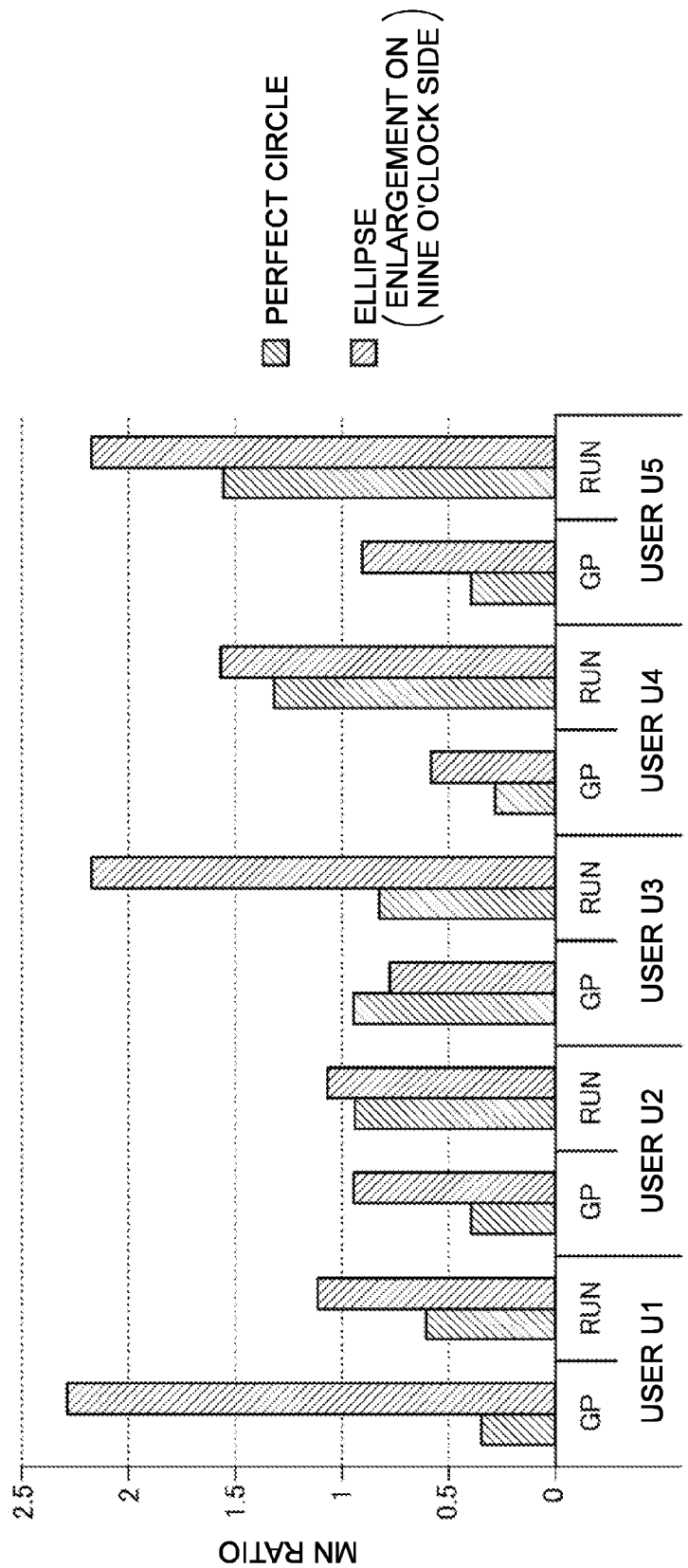
FIG. 15 is a diagram showing the relationship between the shape of a pressing force suppression surface and an MN ratio.
Figure 16:
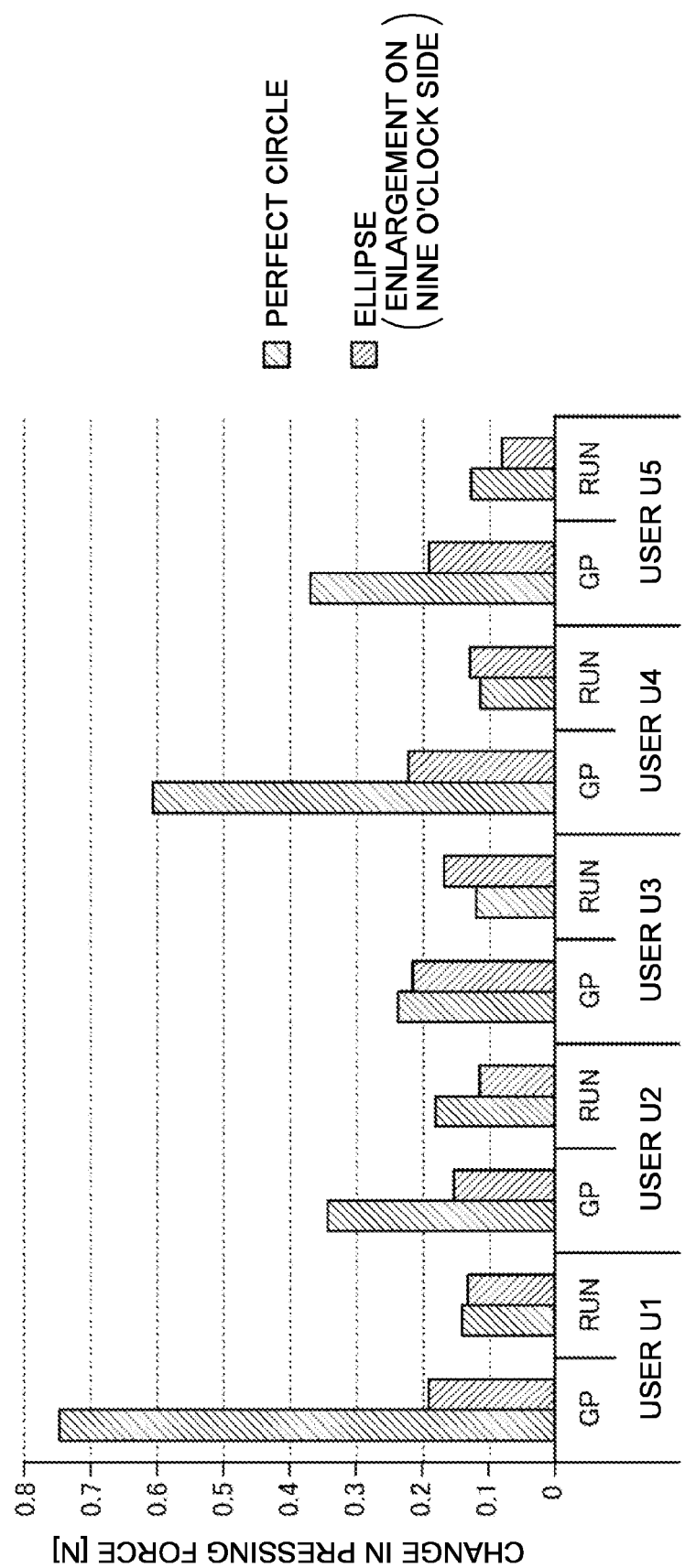
FIG. 16 is a diagram showing the relationship between the shape of the pressing force suppression surface and change in pressing force.

FIGS. 15 and 16 are diagrams showing the relationship between the shape of the pressing force suppression surface 62, and the MN ratio and change in pressing force. For example, FIGS. 15 and 16 are comparison diagrams of the MN ratio or change in pressing force when the user performs a clasp and unclasp operation (GP) or a run operation (RUN) and the pressing force suppression surface 62 is, for example, a perfect circular shape and when the pressing force suppression surface 62 has an elliptical shape (pseudo elliptical shape, track shape) as in this embodiment.

As shown in FIGS. 15 and 16, for many users, the MN ratio becomes higher and change in pressing force becomes smaller when the pressing force suppression surface 62 has an elliptical shape which expands toward the nine o'clock side as shown in FIG. 13 than when the pressing force suppression surface 62 has a perfect circular shape.

For example, when the pressing force suppression surface 62 has a perfect circular shape, the contact surface may come into contact with the radius or the ulna to make it difficult to sufficiently apply the initial pressing force, or the area of the contact surface decreases to make it not possible to sufficiently suppress the pressing force of the convex portion 40 in the use range.

In this regard, as in this embodiment, the contact surface expands toward the second direction DR2 (nine o'clock side), whereby change in load in the convex portion 40 decreases and change in pressing force decreases. As a result, the MN ratio (the magnitude of a power spectrum of a pulse component/the magnitude of a power spectrum of a noise component) which represents quality of the pulse wave detection signal increases.

Figure 17A:
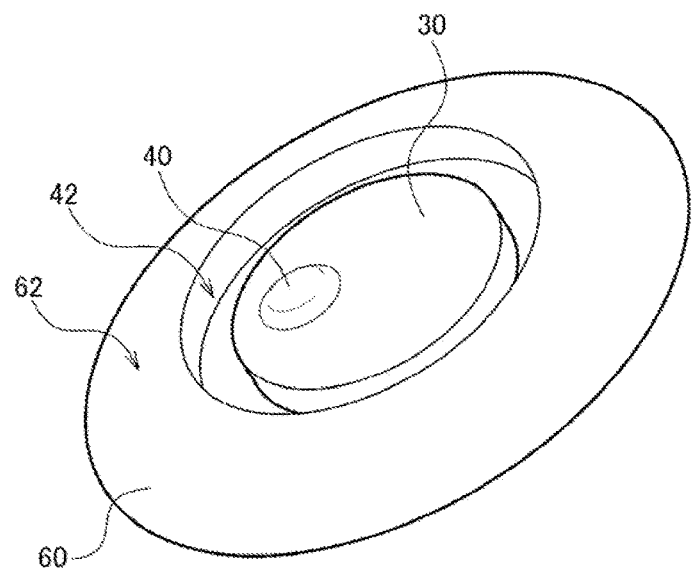
FIGS. 17A to 17C show a modification of the pressing force suppression unit.
Figure 17B:
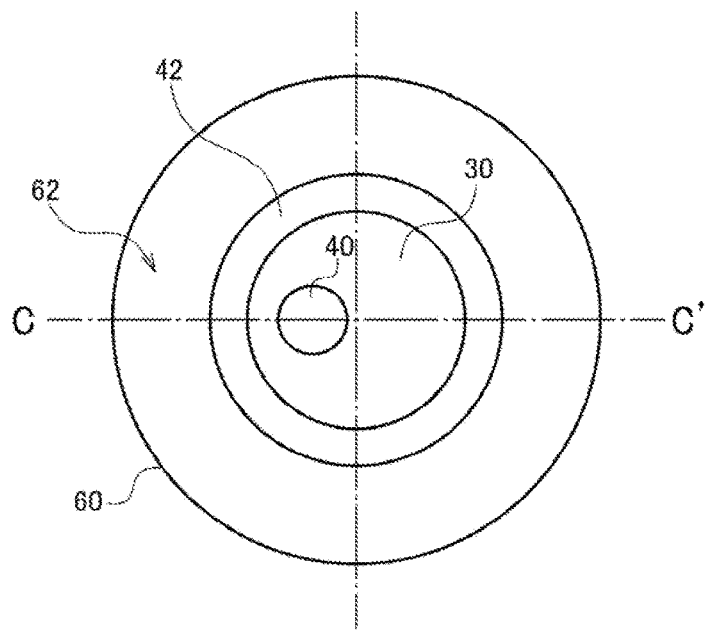
Figure 17C:
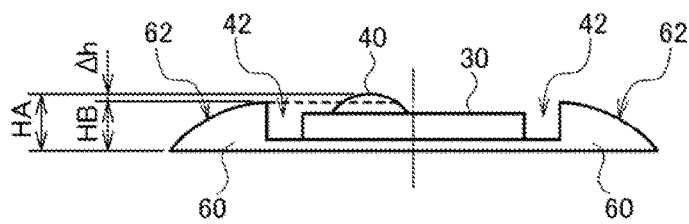

FIGS. 17A to 17C show a modification of the pressing force suppression unit 60. FIG. 17A is a perspective view showing a modification, FIG. 17B is a top view, and FIG. 17C is a sectional view taken along the line C-C' of FIG. 17B.

In this modification, while the convex portion 40 is provided in the light transmitting member 30, and the convex portion 40 is provided at a position deviated from the center position of the light transmitting member 30. While the pressing force suppression unit 60 is provided through the groove portion 42 around the convex portion 40, the shape or structure of the pressing force suppression unit 60 (pressing force suppression surface) is different from that shown in FIGS. 13 and 14. For example, in a top view of FIG. 17B, the pressing force suppression unit 60 has a donut shape (concentrically circular shape) which surrounds the light transmitting member 30 or the convex portion 40.

In this modification, as shown in FIG. 17C, similarly to FIG. 14, the pressing force suppression surface 62 is inclined such that the height in a direction orthogonal to the housing surface decreases outward from the position of the convex portion 40. When the height of the convex portion 40 is referred to as HA, and the height of the pressing force suppression unit 60 is referred to as HB (the height at the highest location), the relationship of Δh=HA−HB>0 is established.

In this way, in regard to the shape or structure of the pressing force suppression unit 60, various modifications may be made. For example, when the biological information detection apparatus is put on a region other than the wrist, it is not necessary that, as in FIG. 13, the convex portion 40 is provided in the first region RG1 on the hand side.

For example, when the inclination as shown in FIG. 17C or the like is provided, the pressing force suppression surface 62 may not be the surface which expands from the position of the convex portion 40 in the second direction DR2. That is, a predetermined direction as a direction in which the inclination is provided is not limited to the second direction DR2. The pressing force suppression surface 62 may not be a surface which is continuous in at least three directions (the first, second, and third directions DR1, DR2, and DR3) around the convex portion 40, and is not necessarily a surface which is continuous over the entire circumference (four directions).

In FIGS. 4, 13, 14, and the like, although the surface of the cover member 20 is molded in a bank shape to form the pressing force suppression unit 60, this embodiment is not limited thereto. For example, various modifications may be made, in which the pressing force suppression unit 60 is formed by a member different from the cover member 20 and is arranged on the housing surface 22.

6. Concave Portion

As described referring to FIGS. 3 and 4, the biological information detection apparatus of this embodiment has the detection unit 130 which has the light receiving unit 140 receiving light from the subject, and the light transmitting member 30 which is provided on the housing surface 22 side in contact with the subject of the biological information detection apparatus, and transmits light entering the light receiving unit 140 from the subject.

Figure 18A:
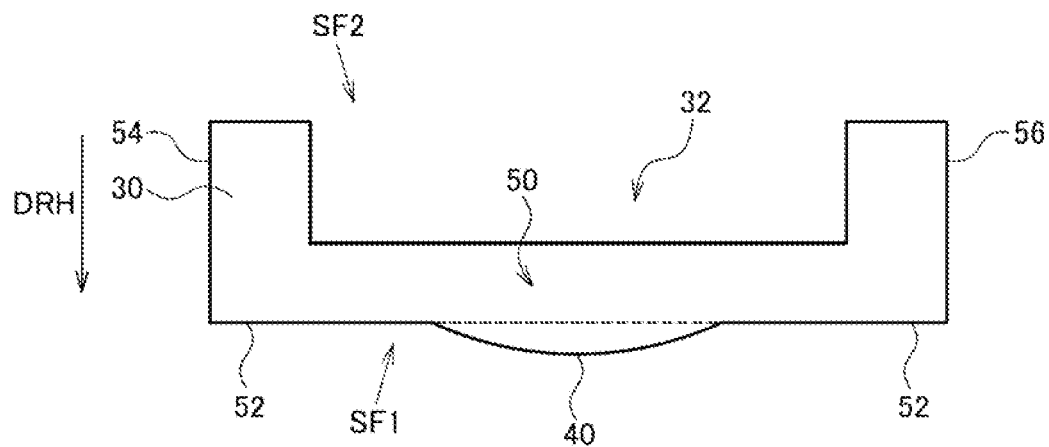
FIGS. 18A and 18B are explanatory views of a method of this embodiment in which a concave portion is provided.

As shown in FIG. 18A, the light transmitting member 30 has the convex portion 40, which comes into contact with the subject when measuring the biological information of the subject to give the pressing force, on a first surface SF1. The light transmitting member 30 has the concave portion 32 at a position corresponding to the convex portion 40 on a second surface SF2 on the rear side of the first surface SF1. The first surface SF1 is the surface (the surface facing the subject) of the light transmitting member 30 on the subject side, and the second surface SF2 is the surface (the surface facing the detection unit) of the light transmitting member 30 on the detection unit side.

For example, a plan view when the convex portion 40 is viewed from the subject in the direction DRH orthogonal to the housing surface 22 in FIGS. 3 and 4 is considered. The concave portion 32 is formed in the light transmitting member 30 so as to overlap the convex portion 40 in a plan view. Specifically, in a plan view when the convex portion 40 is viewed from the subject, when the appearance of the convex portion 40 has a circular shape (substantially circular shape), the appearance of the concave portion 32 has a concentrically (substantially concentrically) circuit shape (substantially circular shape) of the convex portion 40. The radius of the circular shape of the concave portion 32 is greater than the radius of the circular shape of the convex portion 40. However, the appearance shape of the convex portion 40 or the concave portion 32 is not limited to a circular shape (perfect circular shape or elliptical shape), and various modifications may be made. For example, in the above-described plan view, the appearance shape of the convex portion 40 and the concave portion 32 may have a similar shape (substantially similar shape) which is a shape (for example, a triangular shape, a quadrangular shape, or the like) other than a circular shape.

Figure 18B:
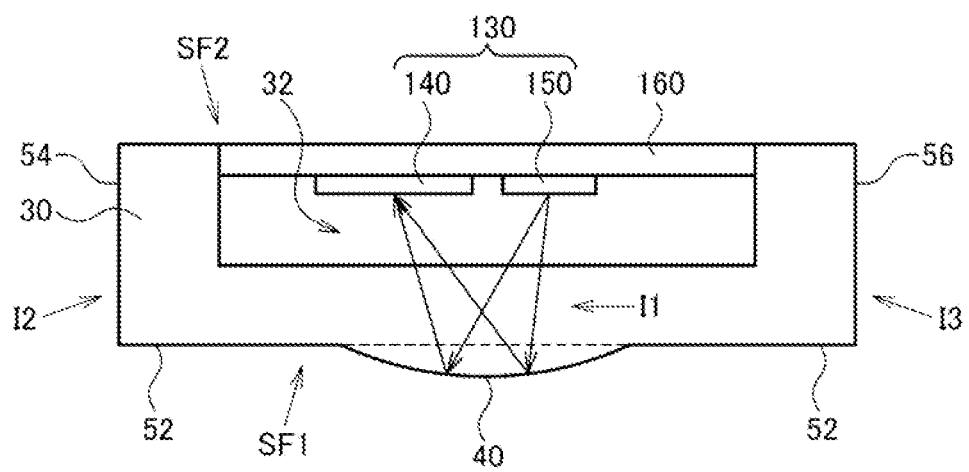

As shown in FIG. 18B, the light receiving unit 140 of the detection unit 130 receives light from the subject which passes through the convex portion 40 and the concave portion 32 of the light transmitting member 30. When the detection unit 130 has the light emitting unit 150 which emits light to the subject, the light emitting unit 150 emits light which passes through the convex portion 40 and the concave portion 32 of the light transmitting member 30. That is, out of the respective portions of the light transmitting member 30, the concave portion 32 is formed in a portion which becomes an optical path of the subject and the light receiving unit 140 or the light emitting unit 150.

If the concave portion 32 is formed in the light transmitting member 30, as indicated by I1 of FIG. 18B, it is possible to shorten an optical path when incoming light to the light receiving unit 140 or outgoing light from the light emitting unit 150 passes through the light transmitting member 30. That is, it is possible to thin the substantial thickness of the light transmitting member 30, and to shorten the passing distance of light in the light transmitting member 30. In this way, if the passing distance of light in the light transmitting member 30 is shortened, since it is possible to increase substantial transmittance of light or to decrease the amount of attenuation of light when light passes through the light transmitting member 30, it is possible to suppress a decrease in the amount of received light of the light receiving unit 140 or the like. Accordingly, it is possible to suppress a decrease in signal component of the pulse wave detection signal since light passes through the light transmitting member 30, and to maintain signal quality of the pulse wave detection signal.

According to a method of forming the concave portion 32 on the second surface SF2 of the light transmitting member 30, as indicated by I2 and I3 of FIG. 18B, in regard to the thickness (the height in the DRH direction) of lateral surfaces 54 and 56 of the light transmitting member 30, it is not necessary to thin the thickness, and it is possible to maintain the thickness. That is, in a portion indicated by I1 of FIG. 18B, while the thickness of the light transmitting member 30 is thinned, and in regard to the lateral surfaces 54 and 56, it is possible to ensure the same thickness as when the concave portion 32 is not formed.

Accordingly, when the location indicated by I2 and I3 of FIG. 18B is the interface of the light transmitting member 30 and a different member (for example, the cover member), it is possible to extend the length of the interface, and to improve waterproof performance or the like. For example, if the thickness of the lateral surfaces 54 and 56 is thinned, and the length of the interface in I2 and I3 is shortened, for example, there is a situation in which a liquid, such as water, intrudes inside the biological information detection apparatus through the interface, causing failure of the detection unit 130 or the like. In this regard, as in this embodiment, according to a method which forms the concave portion 32 in the light transmitting member 30 to ensure the thickness of the lateral surfaces 54 and 56, since it is possible to extend the length of the interface, a liquid, such as water, is less likely to intrude, thereby improving waterproof performance or the like.

It is possible to ensure the thickness of the lateral surfaces 54 and 56, having advantage of maintaining rigidity of the light transmitting member 30. That is, in the entire portion of the light transmitting member 30, if thickness is thin as indicated by I1 of FIG. 18B, rigidity of the light transmitting member 30 may not be sufficiently ensured. In this regard, as in this embodiment, according to a method which forms the concave portion 32 on the second surface SF2 of the light transmitting member 30 to ensure the thickness of the lateral surfaces 54 and 56, it becomes possible to maintain rigidity by the thickness of the lateral surfaces 54 and 56, and to minimize degradation in rigidity of the light transmitting member 30.

If the concave portion 32 is provided on the second surface SF2 of the light transmitting member 30, as shown in FIG. 18B, a product unit having the detection unit 130 and a substrate 160, on which the detection unit 130 is mounted, is fitted in the space of the concave portion 32, thereby completing a pulse wave sensor unit of a biological information detection apparatus. Accordingly, ease of assembling of a product is improved, and reduction in assembling time or cost is achieved.

Figure 25:
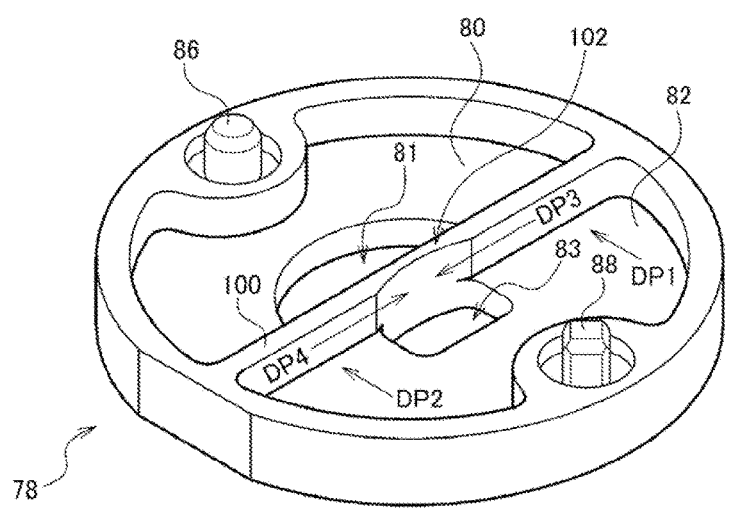
FIG. 25 is a perspective view of a light shielding member in which the diaphragm unit and the light shielding unit are formed integrally.

In particular, as shown in FIG. 25 described below, a method which integrally forms the diaphragm units 80 and 82 and the light shielding unit 100 as a light shielding member 78 is used, thereby further improving ease of assembling. That is, the light shielding member 78 of FIG. 25 is attached from the top (the direction DRH) of the substrate 160 toward the substrate 160, whereby a product unit having the diaphragm units 80 and 82, the light shielding unit 100, the detection unit 130, and the substrate 160 is assembled. The assembled product unit is fitted and attached in the space of the concave portion 32 of the light transmitting member 30, thereby completing a pulse wave sensor unit having the diaphragm units 80 and 82, the light shielding unit 100, the detection unit 130, the substrate 160, and the light transmitting member 30. Accordingly, it is possible to significantly improve ease of component assembling of the biological information detection apparatus.

As above, according to the method of this embodiment which forms the concave portion 32 on the second surface SF2 of the light transmitting member 30, as indicated by I1 of FIG. 18B, the thickness of the light transmitting member 30 at a location corresponding to the convex portion 40 is thin to suppress the amount of attenuation of light, thereby suppressing deterioration of signal quality of a detection signal, and the thickness of the lateral surfaces 54 and 56 is ensured, making it possible to improve waterproof performance or rigidity. That is, it is possible to realize both suppression of deterioration of signal quality of a detection signal and improvement of waterproof performance or rigidity. It also becomes possible to attach the detection unit 130, the diaphragm units 80 and 82, the light shielding unit 100, and the like using the space of the concave portion 32, and to improve ease of assembling.

As the shape or structure of the light transmitting member 30, various modifications may be made. For example, FIGS. 18A and 18B show an example where the convex portion 40 is formed on the first surface SF1 of the light transmitting member 30, and the flat portion 52 is formed around the convex portion. That is, in FIG. 4, although the groove portion 42 is provided around the convex portion 40, in FIGS. 18A and 18B, the groove portion 42 is not provided, and only the flat portion 52 is provided. For example, the height of the flat portion 52 becomes equal to the height of the pressing force suppression unit 60.

Figure 19:
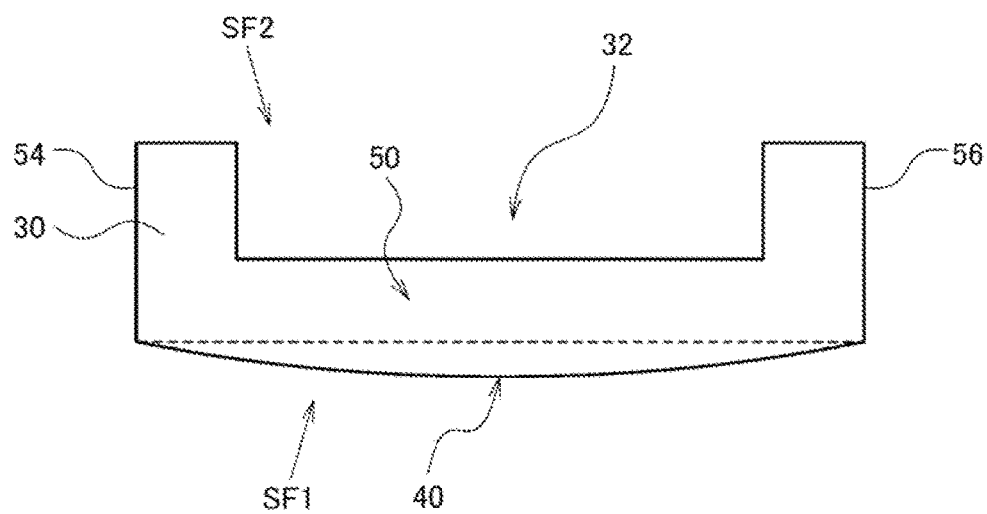
FIG. 19 is an explanatory view showing an example of the light transmitting member.

In FIG. 19, the flat portion 52 of FIGS. 18A and 18B is not provided, and the convex portion 40 is formed on the entire first surface SF1 of the light transmitting member 30. That is, the contact surface (exposed portion) with the subject is entirely formed by the convex portion 40 having a curved shape. That is, in FIGS. 18A and 18B, although the contact surface is formed by the convex portion 40 having a curved shape and the flat portion 52, in FIG. 19, the contact surface is entirely formed only by the convex portion 40 having a curved shape.

For example, according to the method which forms the convex portion 40 on the entire first surface SF1 as shown in FIG. 19, it becomes easy to increase the radius of curvature of the curved shape of the convex portion 40 compared to the method which provides the flat portion 52 as in FIGS. 18A and 18B. The radius of curvature of the convex portion 40 increases, making it possible to efficiently give the pressing force under the condition of the radius of curvature when the contact state with the surface of the subject is stable, and to stabilize signal quality of the pulse wave detection signal.

In this embodiment, as shown in FIGS. 18A to 20A, the light transmitting member 30 has the convex portion 40 and a body portion 50. The convex portion 40 is at least a part of the light transmitting member 30 protrudes (is exposed) toward the subject, and in FIGS. 18A to 20A, the convex portion 40 has a curved shape. In this way, the contact surface of the light transmitting member 30 which comes into contact with the skin of a human is constituted by the convex portion 40 having a curved shape, such that the degree of adhesion of the light transmitting member 30 to the surface of skin is improved. For this reason, it is possible to prevent intrusion of noise light, such as the amount of reflected light from the surface of skin or ambient light. The convex portion 40 may have a shape other than the curved shape.

The body portion 50 is provided on the downward side (in the drawing, the upward side) of the convex portion 40 which is the side (detection unit side) opposite to the subject. The body portion 50 is the main body of the light transmitting member 30, and the convex portion 40 for coming into contact with the subject is formed as the body portion 50 as a main body.

The concave portion 32 is provided on the second surface SF2 of the body portion 50. That is, the convex portion 40 is formed on the first surface SF1 side of the body portion 50, and the concave portion 32 is formed on the second surface SF2 side. With this, it is possible to form the concave portion 32 effectively using the second surface SF2 of the body portion 50.

In this embodiment, as shown in FIG. 20A, the groove portion 42 is provided around the convex portion 40. The bottom surface of the groove portion 42 becomes the surface of the light transmitting member 30. That is, the bottom surface of the groove portion 42 is formed by a part of the surface of the light transmitting member 30 on the subject side. With this configuration, it becomes possible to form the groove portion 42 for improving the MN ratio effectively using the surface of a part of the light transmitting member 30. The height of the bottom surface of the groove portion 42 becomes smaller than the height (the height in the highest end portion) of the pressing force suppression surface 62, and the bottom surface of the groove portion 42 becomes a surface downward (detection unit side) of the pressing force suppression surface 62.

Specifically, the bottom surface of the groove portion 42 becomes the surface of the body portion 50. That is, the bottom surface of the groove portion 42 is formed by a part of the surface on the subject side of the body portion 50 of the light transmitting member 30. With this configuration, it becomes possible to form the groove portion 42 effectively using the surface of a part of the body portion 50 of the light transmitting member 30.

As indicated by E1 of FIG. 20B, the body portion 50 is formed to extend downward of the cover member 20 of the housing surface from the position of the convex portion 40. The pressing force suppression surface 62 is formed by the surface of the cover member 20.

That is, as in FIGS. 3 and 4, the rear lid of the biological information detection apparatus is formed by the light transmitting member 30 and the cover member 20 provided so as to cover the light transmitting member 30. Out of the light transmitting member 30, a portion which is not covered with the cover member 20 becomes a detection window of the pulse wave sensor, and the convex portion 40 is formed in the detection window.

With this structure, it becomes possible to improve waterproof performance, and to prevent a situation in which, for example, a liquid, such as water, intrudes inside the biological information detection apparatus and causes failure of the detection unit 130 or the like. That is, for example, if a structure is made, in which the body portion 50 is cut at a portion indicated by E2 of FIG. 20B, instead of extending the body portion 50, a liquid, such as water, may enter the cut portion, and waterproof performance may be degraded.

In this regard, at E1 of FIG. 20B, since the body portion 50 is formed to extend downward of the cover member 20, there is no intrusion path of the liquid in the portion indicated by E2, thereby significantly improving waterproof performance or the like.

In FIG. 20B, the cover member 20 which covers the extended body portion 50 of the light transmitting member 30 is effectively used to form the pressing force suppression surface 62. With this, it becomes possible to realize both improvement of waterproof performance or the like and improvement of signal quality by pressing force suppression.

7. Diaphragm Unit, Light Shielding Unit

In the biological information detection apparatus of this embodiment, in the light transmitting member 30, a surface which comes into contact with skin as the subject becomes a contact surface having a finite area. In this embodiment, for example, a relatively soft subject, such as skin, comes into contact with the contact surface having a finite area of the light transmitting member 30 formed of a hard material, such as resin or glass. Then, from the viewpoint of theory of elasticity, a region which does not come into contact with skin or a region where a contact pressure is weak occurs near the marginal portion (peripheral portion) of the light transmitting member 30. Even when an external force is applied to the instrument of the biological information detection apparatus, and momentum is generated in the instrument, and a region near the marginal portion of the contact surface is most likely to be steady.

In light passing among the light emitting unit 150, skin, the light receiving unit 140 through this region, light intensity is likely to be optically generated due to change in dynamic contact state. If light enters the light receiving unit 140, light becomes noise having no correlation with a pulse component.

Even in a static contact state, signal quality may be degraded. If there is no proper contact with skin, external light which does not arise from the light emitting unit 150 enters the light receiving unit 140. When the contact pressure is excessive, a subcutaneous blood vessel is crushed, whereby a pulsation component is less brought into light which passes through this region.

As such noise is greatly superimposed, signal quality of the pulse wave detection signal is degraded, and in various kinds of biological measurements, such as pulse measurement, reliability of measured data is degraded.

Figure 21B:
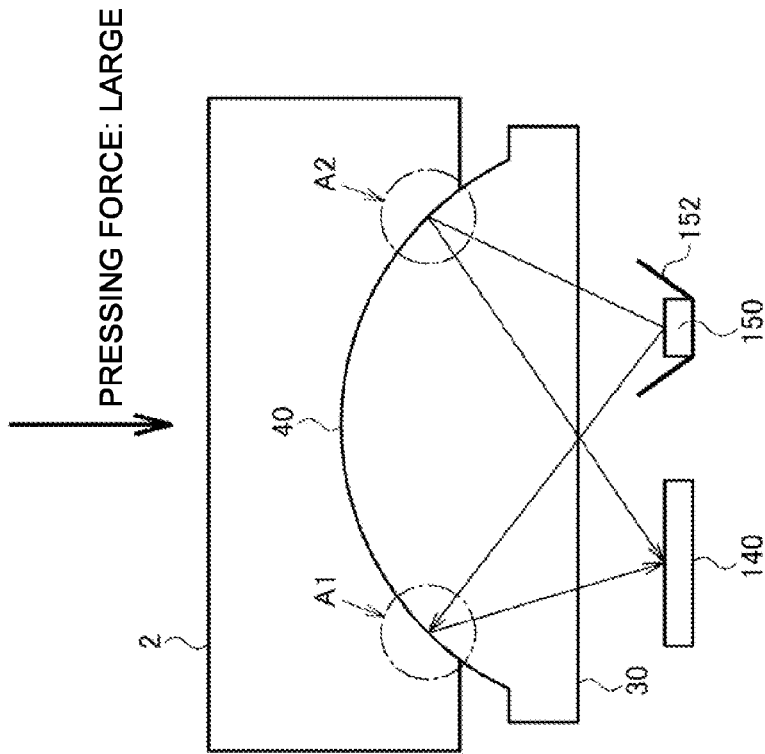
FIGS. 21A and 21B are explanatory views of a problem when a pressing force of the light transmitting member to a subject changes.
Figure 21A:
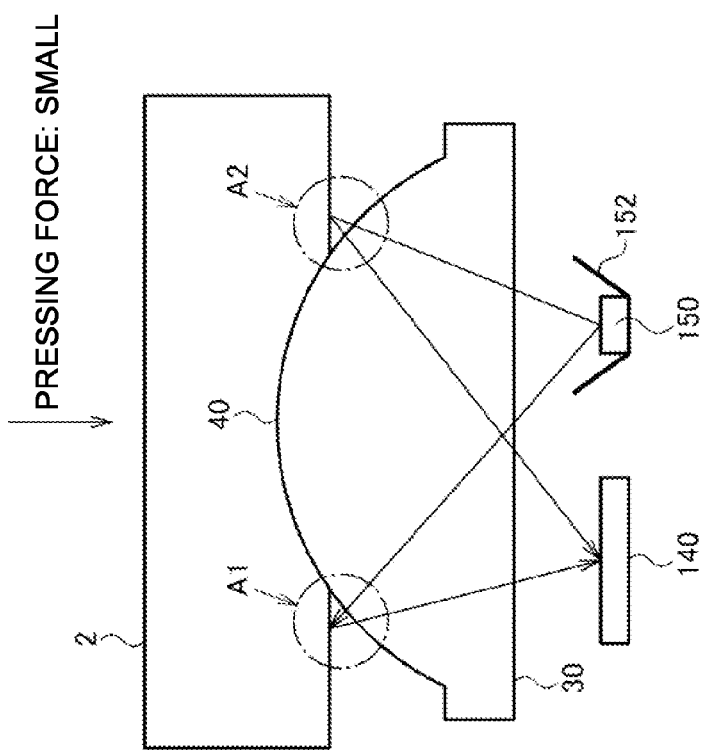

For example, FIG. 21A shows a case where a pressing force given to skin 2 as the subject by the convex portion 40 (contact surface) of the light transmitting member 30 is small, and FIG. 21B shows a case where the pressing force is large. Focusing on the locations indicated by A1 and A2 shown in FIGS. 21A and 21B, change in pressing force causes change in the contact state between the skin 2 and the convex portion 40. For example, in FIG. 21A, while the skin 2 and the convex portion 40 are in a non-contact state or a weak contact state at the locations of A1 and A2, in FIG. 21B, the skin 2 and the convex portion 40 are in the contact state. Accordingly, intensity or the like of light which is emitted from the light emitting unit 150 and returns to the light receiving unit 140 changes between FIGS. 21A and 21B, and reliability of measured data is degraded. FIGS. 21A and 21B may be interpreted as an enlarged view of the periphery of the concave portion 32 in the sectional view of the biological information detection apparatus taken along the line A-A' shown in FIG. 3, or may be interpreted as a projection diagram or an arrangement diagram in which the components in the periphery of the concave portion 32 are projected from the vertical direction with respect to the direction DRH. Hereinafter, although this embodiment will be described using similar diagrams of FIGS. 21A and 21B, it is assumed that all drawings can be interpreted in the same manner.

Figure 22A:
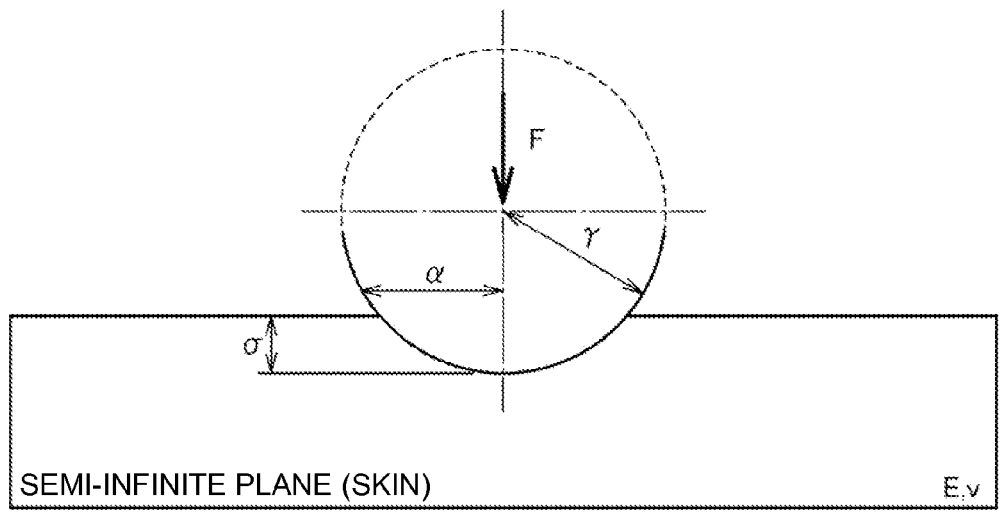
FIGS. 22A and 22B are explanatory views of Hertz elastic contact theory.
Figure 22B:
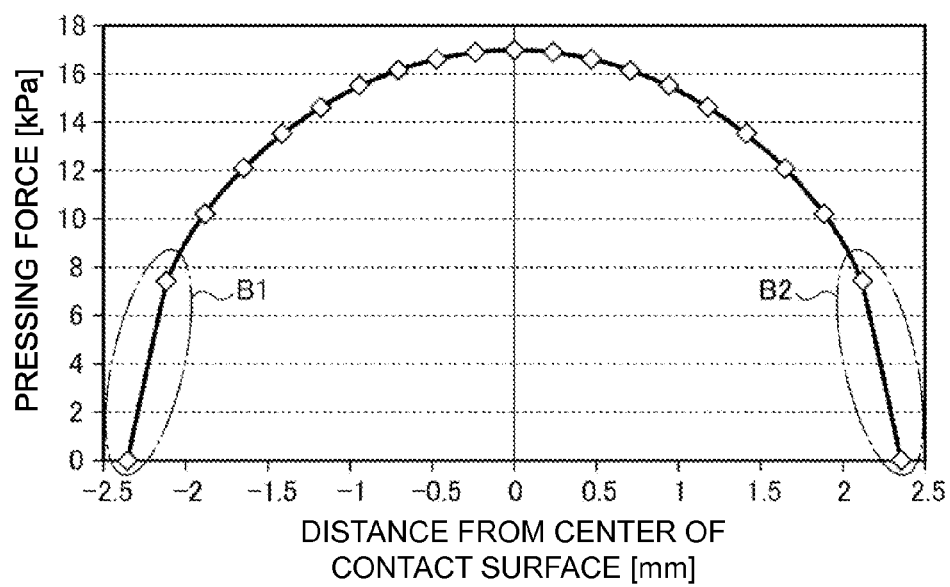

For example, FIGS. 22A and 22B are diagrams illustrating Hertz elastic contact theory. E is a Young's modulus of skin, v is a Poisson's ratio of skin, F is a maximum value of a force to be applied, r is a spherical radius, $\alpha$ is a radius of a contact round surface, and $\sigma$ is a displacement. If predetermined values are substituted in these parameters, and the pressing force with respect to the distance from the center of the contact surface is calculated on the basis of Hertz elastic contact theory, for example, a result shown in FIG. 22B is obtained. As shown in FIG. 22B, if the distance from the center of the contact surface increases, the pressing force decreases, and for example, in the portions indicated by B1 and B2, the pressing force abruptly decreases. Accordingly, at the locations indicated by A1 and A2 of FIGS. 21A and 21B, slight change in load causes abrupt change in the pressing force on the contact surface, and reliability of measured data is significantly degraded.

For example, in FIGS. 21A and 21B, the contact surface of the light transmitting member 30 which comes into contact with skin of a human has a curved convex shape (convex portion). With this, since the degree of adhesion of the light transmitting member 30 to the surface of skin is improved, it is possible to prevent intrusion of noise light, such as the amount of reflected light from the surface of skin or ambient light.

However, as will be apparent from FIGS. 22A and 22B, in the marginal portion (peripheral portion) of the convex shape, the contact pressure with skin relatively decreases with respect to the center portion.

In this case, if optimization is made with the contact pressure of the center portion, the contact pressure of the marginal portion is less than an optimum range. If optimization is made with the contact pressure of the marginal portion, the contact pressure of the center portion is excessive with respect to the optimum range.

When the contact pressure is less than the optimum range, in a case where the pulse wave sensor comes into contact with skin or is detached from skin due to shaking of the apparatus, or even if the pulse wave sensor is in contact with skin, the pulse wave sensor does not crush the vein completely, whereby body motion noise is superimposed on the pulse wave detection signal. If the noise component is reduced, it becomes possible to obtain a pulse wave detection signal having a higher M/N ratio (S/N ratio).

In order to solve the above-described problem, as shown in FIGS. 4, 23A, and 23B, in this embodiment, the diaphragm units 80 and 82 (aperture) are provided. The diaphragm units 80 and 82 narrow light from the subject in the optical path between the subject and the detection unit 130. In FIG. 4 and the like, the detection unit 130 has the light emitting unit 150 which emits light to the subject, and the light transmitting member 30 transmits light from the light emitting unit 150. The diaphragm units 80 and 82 narrow light from the light emitting unit 150 in the optical path between the subject and the detection unit 130. A reflector 152 reflects light emitted from the light emitting unit 150 to increase light use efficiency.

In this way, in this embodiment, the diaphragm units 80 and 82 are provided such that light (stray light) at the locations or the like indicated by A1 and A2 of FIGS. 23A and 23B is not detected, and narrow light. For example, light which passes through the center portion (for example, the vertex of the convex portion) of the light transmitting region of the light transmitting member 30 with an optimum pressing force is transmitted as much as possible without being shielded, and light near the marginal portion of the light transmitting region (for example, the convex portion) of the light transmitting member 30 is shielded. For example, in FIGS. 23A and 23B, the diaphragm unit 80 is provided such that light at the location indicated by A1 in the marginal portion does not enter the light receiving unit 140. The diaphragm unit 82 is provided such that light from the light emitting unit 150 is not emitted to the location indicated by A2. That is, in this embodiment, light at a location where change in pressing force (load) causes change in the contact state is narrowed. With this configuration, as shown in FIGS. 23A and 23B, even when the contact state changes at the locations indicated by A1 and A2, the states of light at the locations indicated by A1 and A2 do not affect a light receiving result. Accordingly, it is possible to improve reliability of measured data or the like.

In FIGS. 4, 23A, 23B, and the like, the light shielding unit 100 (light shielding wall) is provided between the light receiving unit 140 the light emitting unit 150. The light shielding unit 100 is, for example, a light shielding wall which is formed to extend in the direction DRH orthogonal to the housing surface 22 (see FIGS. 3 and 4). Specifically, for example, the light shielding unit 100 which has a wall surface along a direction intersecting (orthogonal to) a line segment connecting the center position of the light receiving unit 140 and the center position of the light emitting unit 150 is provided. The light shielding unit 100 is provided such that the entrance of direct light from the light emitting unit 150 to the light receiving unit 140 is inhibited, thereby further improving reliability of measured data or the like.

That is, as the distance between the light receiving unit 140 and the light emitting unit 150 decreases, optical efficiency or performance is improved. For example, optical efficiency or performance is deteriorated in inverse proportion to the square of the distance. Accordingly, it is preferable to decrease the distance between the light receiving unit 140 and the light emitting unit 150 as small as possible.

However, if the distance between the light receiving unit 140 and the light emitting unit 150 decreases, there is an increasing possibility that direct light from the light emitting unit 150 enters the light receiving unit 140 and performance is deteriorated.

Accordingly, the light shielding unit 100 is provided between the light receiving unit 140 and the light emitting unit 150 to inhibit direct light from the light emitting unit 150 from entering the light receiving unit 140. That is, in this embodiment, as described above, in order to eliminate optical adverse effects from a path in which the contact state of the subject and the contact surface becomes unstable, the diaphragm units 80 and 82 are provided. The adverse effects by direct light of the light emitting unit 150 are eliminated by the light shielding unit 100. With this configuration, it becomes possible to ensure optical stability of a photoelectric pulse wave sensor by the diaphragm units 80 and 82 which eliminate noise due to change in the contact state of the subject and the contact surface, and the light shielding unit 100 which eliminates direct light of the light emitting unit 150. The light shielding unit 100 may not be provided.

In FIGS. 4, 23A, 23B, and the like, the diaphragm units 80 and 82 are provided between the light transmitting member 30 and the detection unit 130 (light receiving unit 140, light emitting unit 150). For example, the diaphragm units 80 and 82 are arranged and set at the positions away from the light transmitting member 30 or the detection unit 130. In this way, if the diaphragm units 80 and 82 are arranged between the light transmitting member 30 and the detection unit 130, stray light is effectively shielded by the diaphragm units 80 and 82 on the optical path between the subject and the detection unit 130, thereby effectively suppressing a situation in which noise due to stray light is superimposed on measured data. However, the method of arranging and setting the diaphragm units 80 and 82 is not limited thereto, various modifications may be made, and the diaphragm units 80 and 82 may be provided between the light transmitting member 30 and the subject or inside the light transmitting member 30.

Figure 24A:
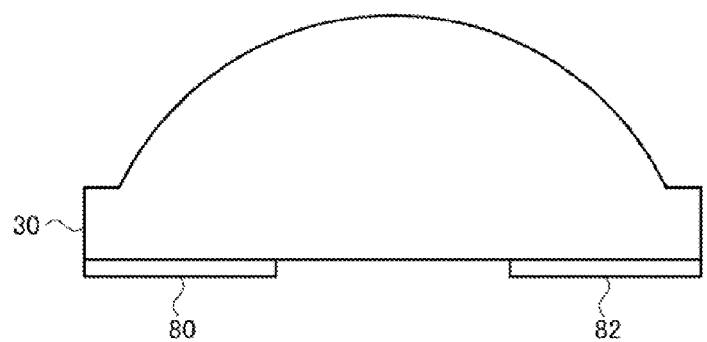
FIGS. 24A to 24C are diagrams showing various examples of an arrangement position of the diaphragm unit.
Figure 24B:
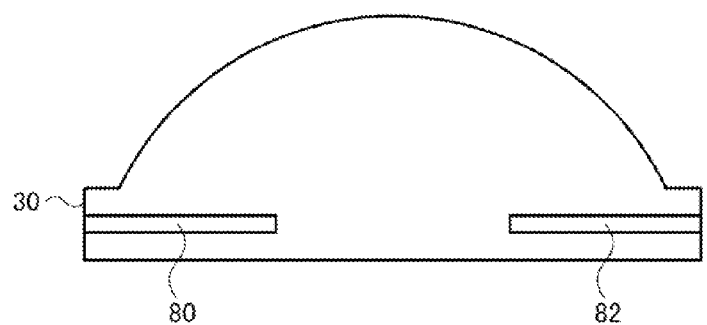
Figure 24C:
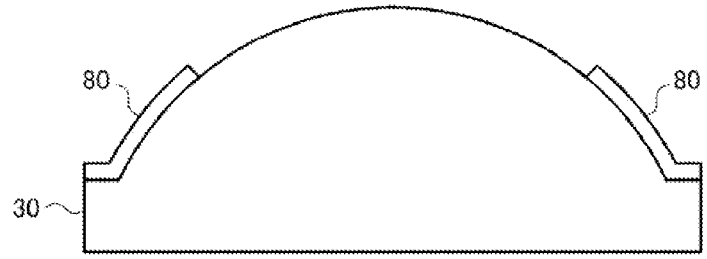

For example, in FIG. 24A, while the diaphragm units 80 and 82 are provided between the light transmitting member 30 and the detection unit 130, the diaphragm units 80 and 82 are arranged and formed so as to be in close contact with the light transmitting member 30. In FIG. 24B, the diaphragm units 80 and 82 are arranged and formed inside the light transmitting member 30 (in the material). In FIG. 24C, the diaphragm units 80 and 82 are arranged and formed between the subject and the light transmitting member 30. In this way, as the method of arranging and forming the diaphragm units 80 and 82, various forms may be assumed.

A method of manufacturing the diaphragm units 80 and 82 is not limited to a method of forming diaphragm units 80 and 82 separately from the light transmitting member 30 or the like as in FIGS. 4, 23A, 23B, and the like, and various methods may be used. For example, as in FIGS. 24A and 24C, when forming the diaphragm units 80 and 82 so as to be in close contact with the light transmitting member 30, the diaphragm units 80 and 82 may be formed by a method, such as painting, vapor deposition, or printing. Alternatively, as in FIG. 24B, when forming the diaphragm units 80 and 82 in the light transmitting member 30, for example, the diaphragm units 80 and 82 may be formed by a method, such as insert molding.

In this embodiment, the diaphragm units 80 and 82 and the light shielding unit 100 may be integrally formed as the light shielding member 78. That is, the diaphragm units 80 and 82 and the light shielding unit 100 (light shielding wall) have an integral structure. FIG. 25 is a perspective view showing an example of the light shielding member 78 integrally formed in the above-described manner.

As shown in FIG. 25, in the light shielding member 78, the diaphragm unit 80 (first diaphragm unit) provided on the light receiving unit side and the diaphragm unit 82 (second diaphragm unit) provided on the light emitting unit side are formed. An opening 81 of the diaphragm on the light receiving unit side is formed corresponding to the diaphragm unit 80 on the light receiving unit side, and an opening 83 of the diaphragm on the light emitting unit side is formed corresponding to the diaphragm unit 82 on the light emitting unit side. The light shielding unit 100 is formed between the diaphragm units 80 and 82 integrally with the diaphragm units 80 and 82. For example, the light shielding member 78 has a shape of a bottomed tubular portion in which a bottom portion is formed at one end side and the other end is opened, and the bottom portion of the bottomed tubular portion is formed as the diaphragm units 80 and 82. The openings 81 and 83 which function as an aperture are formed for the diaphragm units 80 and 82 in the bottom portion. The light shielding unit 100 is formed so as to bisect (divide) of the region of the opening at the other end of the bottomed tubular portion.

As shown in FIG. 25, the thickness of the light shielding unit 100 becomes thin in the center portion 102. With this, it becomes possible to decrease the distance between the light receiving unit 140 and the light emitting unit 150, and to improve optical efficiency or performance.

The height of the light shielding unit 100 in the direction DRH (see FIG. 5A) orthogonal to the housing surface 22 (see FIGS. 3 and 4) of the biological information detection apparatus is referred to as H1, and the height of the lower surface which is the surface on the detection unit 130 side of each of the diaphragm units 80 and 82 is referred to as H2. The heights H1 and H2 are the height from a reference surface (for example, the substrate 160). In this case, the relationship of H1>H2 is established. That is, the light shielding unit 100 becomes a light shielding wall which is formed to extend to a position higher than the lower surface of the diaphragm units 80 and 82. With this, it is possible to suppress a situation in which light from the light emitting unit 150 is reflected by the diaphragm units 80 and 82 and the like and enters the light receiving unit 140. That is, it becomes possible to eliminate the effect of direct reflected light of the light emitting unit 150, and to suppress degradation in reliability of measured data or the like.

The light shielding member 78 is attached toward the substrate 160 from the top (the direction opposite to the direction DRH) of the substrate 160 on which the light receiving unit 140 and the light emitting unit 150 are mounted (see FIG. 5A). That is, the light shielding member 78 is attached such that the substrate 160 having the light receiving unit 140 and the light emitting unit 150 mounted thereon is inserted into the region of the opening at the other end of the bottomed tubular portion shape of the light shielding member 78. Protrusions 86 and 88 are formed in the light shielding member 78, and the protrusions 86 and 88 are engaged with hole portions formed in the substrate 160, whereby the light shielding member 78 is fixed to the substrate 160. Accordingly, for example, the diaphragm units 80 and 82, the light shielding unit 100, the light receiving unit 140, and the light emitting unit 150 are arranged at a position corresponding to the concave portion 32 on the rear side of the light transmitting member 30. In this case, the thickness of the light transmitting member 30 becomes thin in the portion of the concave portion 32. Accordingly, it is possible to reduce the length of the optical path which is the passing distance of light entering the light receiving unit 140 or light emitted from the light emitting unit 150 in the light transmitting member 30. Accordingly, the attenuation of light in the light transmitting member 30 is reduced, thereby improving the amount of transmitted light.

It is preferable that processing for improving optical efficiency or performance of the pulse wave sensor is performed on the diaphragm units 80 and 82 and the light shielding unit 100. For example, processing for roughening the surface (wall surface) of the diaphragm units 80 and 82 and the light shielding unit 100 is performed, thereby suppressing reflectance of light. Alternatively, the surface of the diaphragm units 80 and 82 and the light shielding unit 100 has a moth eye structure. For example, a rugged structure in a cycle of tens to hundreds of nm is formed on the surface to form a reflection prevention structure. Alternatively, the color of the surface of the diaphragm units 80 and 82 and the light shielding unit 100 is a predetermined color, such as black, thereby preventing irregular reflection of light. With this configuration, it is possible to effectively suppress a situation in which reflected light in the diaphragm units 80 and 82 and the light shielding unit 100 becomes stray light, and stray light becomes the noise component of measured data.

As described above, in order to improve optical efficiency or performance of the pulse wave sensor, it is preferable to minimize the distance between the light receiving unit 140 and the light emitting unit 150. For this reason, it is necessary that the light shielding unit 100 has a wall-thickness structure as thin as possible. In particular, in the center portion 102 (a region intersecting a line which connects the center position of the light receiving unit 140 and the center position of the light emitting unit 150) of the light shielding unit 100 of FIG. 25, the wall thickness of the light shielding unit 100 is thin.

However, in a single structure of the light shielding unit 100 whose wall thickness is thin, strength is lacking. For example, during traveling in which the pulsimeter is used or during cycling, since strong impact (for example, about 10 G) is applied to the apparatus, enough strength to cope with this impact is required.

Accordingly, in FIG. 25, a method of forming the diaphragm units 80 and 82 and the light shielding unit 100 in an integral structure is utilized. That is, each of the diaphragm units 80 and 82 and the light shielding unit 100 is not realized by a single member, and as shown in FIG. 25, the light shielding member 78 in which the diaphragm units 80 and 82 and the light shielding unit 100 are integrally formed is used. With the light shielding member 78 integrally formed, even if the wall thickness of the light shielding unit 100 is thin, it becomes possible to ensure strength enough to bear with impact.

Since the diaphragm units 80 and 82 and the light shielding unit 100 are identical in terms of optical stabilization, the materials are readily shared. For example, it becomes easy to set the color of the surface of the diaphragm units 80 and 82 and the light shielding unit 100 in black so as to suppress the occurrence of irregular reflection.

The diaphragm units 80 and 82 and the light shielding unit 100 are integrally formed, thereby improving ease of assembling during component assembling and contributing to reduction in cost. For example, the light shielding member 78 is inserted into the concave portion 32 of the light transmitting member 30, the protrusions 86 and 88 of the light shielding member 78 are fixed to be engaged with the substrate 160 having the light receiving unit 140 and the light emitting unit 150 mounted thereon, thereby completing assembling of the pulse wave sensor.

Taking the productivity of the apparatus into consideration, it is preferable to manufacture the light shielding member 78 by injection molding. However, if the wall thickness of the light shielding unit 100 is too thin, during injection molding, resin is not sufficiently filled in the portion of the light shielding unit 100.

Accordingly, in FIG. 25, it is configured such that the area of the opening 83 of the diaphragm unit 82 on the light emitting unit side becomes smaller than the area of the opening 81 of the diaphragm unit 80 (first diaphragm unit) on the light receiving unit side.

In FIG. 25, it is configured such that the wall thickness of the light shielding unit 100 is minimized on a line which connects the center of the light receiving unit 140 and the center of the light emitting unit 150. For example, the wall thickness becomes thin toward the center portion 102.

For example, if the area of the opening 83 on the light emitting unit side is small, the paths of DP1 and DP2 of FIG. 25 can be set in the path into which resin flows in injection molding. Resin flows into the path from DP1 to DP3 and the path from DP2 to DP4, whereby resin is sufficiently filled. For this reason, in the center portion 102 whose wall thickness is thin, the light shielding unit 100 can be formed of resin. For example, in general, the size of the light emitting unit 150 which is realized by an LED or the like is smaller than the size of the light receiving unit 140 which is realized by a semiconductor IC or the like of a photodiode. Accordingly, even if the area of the opening 83 on the light emitting unit side is small, there is no problem as much. The area of the opening 81 on the light receiving unit side is large, whereby it is possible to increase light receiving efficiency and to achieve improvement of the performance or the like of the biological information detection apparatus.

In this way, if the area of the opening 83 on the light emitting unit side is small to allow resin to easily flow, and the wall thickness in the center portion 102 of the light shielding unit 100 or the like is thin, it is possible to decrease the distance between the light receiving unit 140 and the light emitting unit 150. Accordingly, it is possible to improve optical efficiency or performance. That is, it becomes possible to prevent resin from being not sufficiently filled during injection molding and to achieve improvement of yield or the like while achieving both strength and optical efficiency or performance of the light shielding unit 100.

8. Overall Configuration of Biological Information Detection Apparatus

Figure 26:
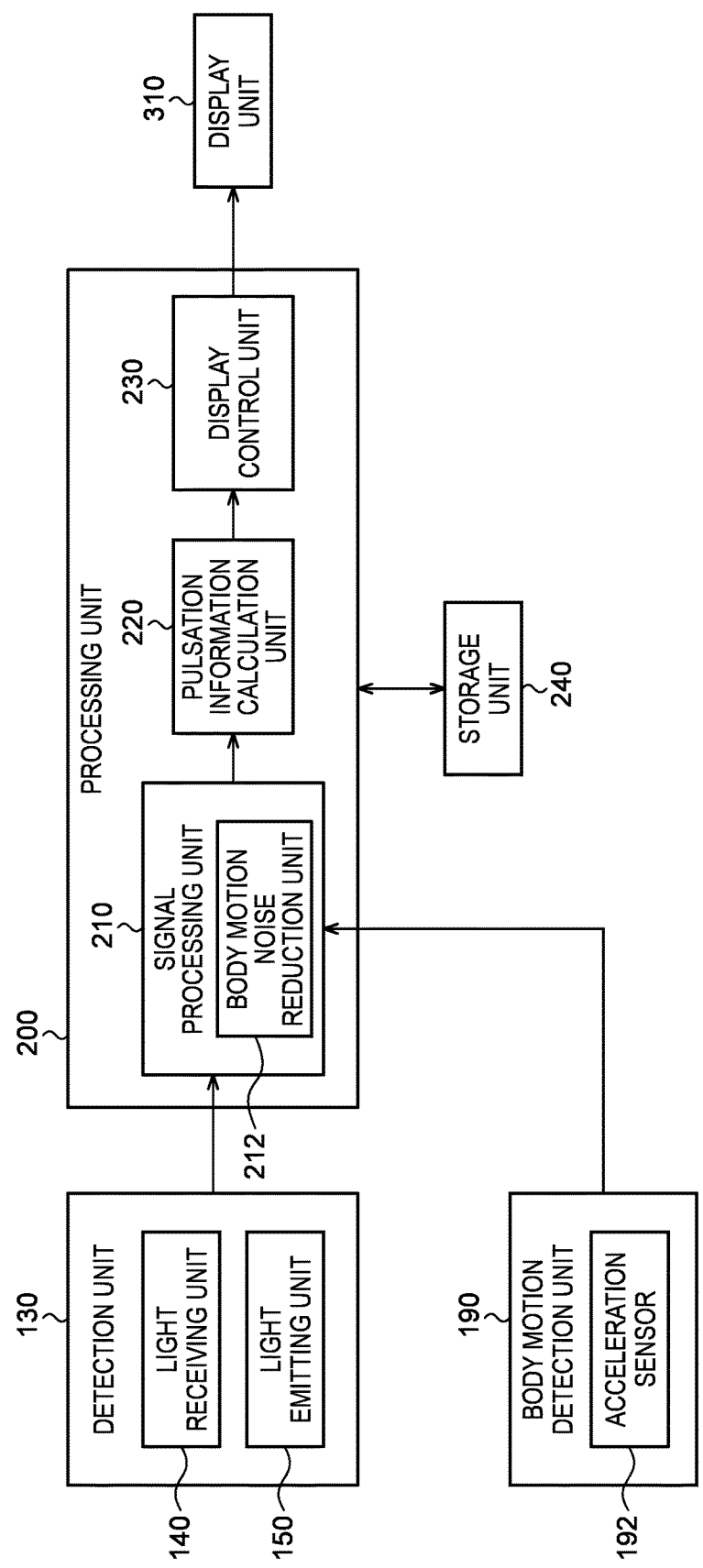
FIG. 26 is a functional block diagram showing an example of the overall configuration of the biological information detection apparatus.

FIG. 26 is a functional block diagram showing an example of the overall configuration of the biological information detection apparatus. The biological information detection apparatus of FIG. 26 includes the detection unit 130, a body motion detection unit 190, a processing unit 200, a storage unit 240, and a display unit 310. The biological information detection apparatus of this embodiment is not limited to the configuration of FIG. 26, various modifications in which some of the components are omitted and other components are added may be made.

The detection unit 130 detects biological information, such as a pulse wave, and includes the light receiving unit 140 and the light emitting unit 150. A pulse wave sensor (photoelectric sensor) is realized by the light receiving unit 140, the light emitting unit 150, and the like. The detection unit 130 outputs a signal detected by the pulse wave sensor as a pulse wave detection signal.

The body motion detection unit 190 outputs a body motion detection signal, which is a signal with change according to a body motion, on the basis of sensor information of various sensors. The body motion detection unit 190 includes, for example, an acceleration sensor 192, as a body motion sensor. The body motion detection unit 190 may have a pressure sensor or a gyro sensor as a body motion sensor.

The processing unit 200 performs various kinds of signal processing or control processing with the storage unit 240 as a work area, and can be realized by, for example, a processor, such as a CPU, or a logic circuit, such as an ASIC. The processing unit 200 includes a signal processing unit 210, a pulsation information calculation unit 220, and a display control unit 230.

The signal processing unit 210 performs various kinds of signal processing (filtering and the like), and performs signal processing on, for example, the pulse wave detection signal from the detection unit 130, the body motion detection signal from the body motion detection unit 190, or the like. For example, the signal processing unit 210 includes a body motion noise reduction unit 212. The body motion noise reduction unit 212 performs processing for reducing (eliminating) body motion noise as noise due to a body motion from the pulse wave detection signal on the basis of the body motion detection signal from the body motion detection unit 190. Specifically, for example, noise reduction processing using an adaptive filter or the like is performed.

The pulsation information calculation unit 220 performs calculation processing of pulsation information on the basis of a signal from the signal processing unit 210 or the like. The pulsation information is, for example, information, such as a pulse rate. Specifically, the pulsation information calculation unit 220 performs frequency analysis processing, such as FFT, on the pulse wave detection signal after the noise reduction processing in the body motion noise reduction unit 212 to obtain a spectrum, and performs processing for defining a representative frequency in the obtained spectrum as the frequency of heartbeat. A value 60 times the obtained frequency becomes a pulse rate (heart rate) which is generally used. The pulsation information is not limited to the pulse rate, and for example, various other kinds of information (for example, the frequency, cycle, or the like of heartbeat) representing the pulse rate may be used. Information representing the state of pulsation may be used, and for example, a value representing a blood volume may be used as the pulsation information.

The display control unit 230 performs display control for displaying various kinds of information or images on the display unit 310. For example, as shown in FIG. 1A, control is performed such that various kinds of information including the pulsation information, such as the pulse rate, time information, and the like, are displayed on the display unit 310. Instead of the display unit 310, a notice device which outputs light, sound, vibration, or the like stimulating perception of the user may be provided. As the notice device, for example, an LED, a buzzer, a vibrator, or the like may be assumed.

Although this embodiment has been described above in detail, it can be easily understood by those skilled in the art that many modifications may be made without departing from the new matter and effects of the invention in a substantive way. Accordingly, such modifications still fall within the scope of the invention. For example, in the specification or the drawings, there are some terms which are presented at least once together with other terms which have a broader meaning or the same meaning, and each of these terms can be replaced with the other corresponding term at any location in the specification and the drawings. The configuration and operation of the biological information detection apparatus are not limited to those described in this embodiment, and various modifications may be made.

What is claimed is:

1. A biological information detection apparatus comprising:
    a housing surface;
    a detection unit which has a light receiving unit configured to receive light from a subject;
    a light transmitting member which is provided on the housing surface configured to be in contact with the subject of the biological information detection apparatus, configured to transmit light from the subject, and has a convex portion configured to be in contact with the subject to give a pressing force; and
    a pressing force suppression unit which is provided around an entire circumference of the convex portion to surround the convex portion above the housing surface and configured to suppress the pressing force given to the subject by the convex portion,
    wherein a groove portion is provided between the convex portion of the light transmitting member and the pressing force suppression unit, and
    wherein a height of the convex portion, a height of the pressing force suppression unit, and a height of a bottom surface of the groove portion are respectively HA, HB, and HC, HA>HB>HC, wherein the height of the convex portion extends along a direction orthogonal to the housing surface.

2. The biological information detection apparatus according to claim 1,
    wherein the difference between the height HA of the convex portion and the height HC of the bottom surface of the groove portion is $\Delta h2$, $\Delta h2 > 0.5$ mm.

3. The biological information detection apparatus according to claim 1,
    wherein the groove portion is provided over the entire circumference of the convex portion.

4. The biological information detection apparatus according to claim 1,
wherein the bottom surface of the groove portion is a surface of the light transmitting member.

5. The biological information detection apparatus according to claim 1,
wherein the light transmitting member has
the convex portion at least a part of which is configured to protrude toward the subject, and
a body portion which is provided on the downward side of the convex portion, configured to be opposite to the subject, and
the bottom surface of the groove portion is a surface of the body portion.

6. The biological information detection apparatus according to claim 5, wherein the body portion is formed to extend from the convex portion downward of a cover member of the housing surface, and a pressing force suppression surface of the pressing force suppression unit is a surface of the cover member.

7. The biological information detection apparatus according to claim 1, further comprising:
a load mechanism having a load configured to generate the pressing force given to the subject by the convex portion, wherein an amount of change in the pressing force with respect to the load of the load mechanism is defined as the amount of change in pressing force, and
wherein the amount of change in pressing force in a second load range in which the load of the load mechanism is greater than FL1 becomes smaller than the amount of change in pressing force in a first load range in which the load of the load mechanism is 0 to FL1.

8. The biological information detection apparatus according to claim 1,
wherein the pressing force suppression unit has a pressing force suppression surface which expands outward from around the convex portion.

9. The biological information detection apparatus according to claim 8,
wherein a position away from the convex portion at a first distance in a predetermined direction is a first position, a position away from the convex portion at a second distance longer than the first distance in the predetermined direction is a second position, a height of the pressing force suppression surface in a direction orthogonal to the housing surface at the first position is HS1, and a height of the pressing force suppression surface in the direction orthogonal to the housing surface at the second position is HS2, HS1>HS2.

10. The biological information detection apparatus according to claim 8,
wherein the pressing force suppression surface is inclined, and
a height of the pressing force suppression surface in the direction orthogonal to the housing surface decreases toward a predetermined direction from the convex portion.

11. The biological information detection apparatus according to claim 1, wherein
the detection unit includes a light emitting unit which is configured to emit light to the subject,
the light transmitting member transmits light from the light emitting unit, and
the biological information detection apparatus further comprises:

a light shielding wall which is provided between the light receiving unit and the light emitting unit.

12. The biological information detection apparatus according to claim 1,
wherein a pulse wave is detected as the biological information.

13. A biological information detection apparatus comprising:
a housing surface;
a detection unit which has a light receiving unit configured to receive light from a subject;
a light transmitting member which is provided on the housing surface configured to be in contact with the subject of the biological information detection apparatus, and configured to transmit light entering the light receiving unit from the subject; and
a cover member covering a portion of the light transmitting member, the cover member including a pressing force suppression surface opposite from a surface of the cover member contacting the portion of the light transmitting member,
wherein the light transmitting member has a body portion, a convex portion formed on a first surface of the body portion, and a concave portion formed a second surface of the body portion, wherein the convex portion is configured to come into contact with the subject to give a pressing force, wherein the concave portion is formed at a position corresponding to the convex portion on a rear side of the first surface, wherein the portion of the light transmitting member is adjacent to the body portion.

14. The biological information detection apparatus according to claim 13,
wherein the light receiving unit of the detection unit is configured to receive light from the subject which passes through the convex portion and the concave portion of the light transmitting member.

15. The biological information detection apparatus according to claim 13, wherein
the detection unit has a light emitting unit which is configured to emit light to the subject, and
the light emitting unit emits light which passes through the convex portion and the concave portion of the light transmitting member.

16. The biological information detection apparatus according to claim 13,
wherein the light transmitting member has a flat portion formed around the convex portion on the first surface.

17. The biological information detection apparatus according to claim 13,
wherein the convex portion is formed on the entire first surface of the body portion of the light transmitting member.

18. The biological information detection apparatus according to claim 13, further comprising:
a pressing force suppression unit which is provided around an entire circumference of the convex portion to surround the convex portion above the housing surface and configured to suppress the pressing force given to the subject by the convex portion.

19. The biological information detection apparatus according to claim 13, wherein
the light transmitting member has
the convex portion at least a part of which is configured to protrude toward the subject, and a body portion which is configured to be provided on a downward side of the convex portion opposite to the subject, and the convex portion is provided on the second surface of the body portion.

* * * * *